US011553899B2

United States Patent
Honjo et al.

(10) Patent No.: US 11,553,899 B2
(45) Date of Patent: Jan. 17, 2023

(54) ANALYSIS APPARATUS

(71) Applicant: Canon Medical Systems Corporation, Otawara (JP)

(72) Inventors: Yasunori Honjo, Utsunomiya (JP); Masaki Watanabe, Utsunomiya (JP); Yu Igarashi, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 511 days.

(21) Appl. No.: 16/398,345

(22) Filed: Apr. 30, 2019

(65) Prior Publication Data

US 2019/0254634 A1 Aug. 22, 2019

Related U.S. Application Data

(63) Continuation of application No. PCT/JP2018/047963, filed on Dec. 26, 2018.

(30) Foreign Application Priority Data

Dec. 27, 2017 (JP) .............................. JP2017-252111

(51) Int. Cl.
*A61B 5/055* (2006.01)
*A61B 6/03* (2006.01)
*A61B 8/00* (2006.01)
*A61B 8/08* (2006.01)
*A61B 5/00* (2006.01)
(Continued)

(52) U.S. Cl.
CPC .............. *A61B 8/485* (2013.01); *A61B 5/055* (2013.01); *A61B 5/4244* (2013.01); *A61B 6/03* (2013.01); *A61B 6/032* (2013.01); *A61B 8/08* (2013.01); *A61B 8/0858* (2013.01); *A61B 8/463* (2013.01); *A61B 8/469* (2013.01); *A61B 8/5223* (2013.01);
(Continued)

(58) Field of Classification Search
CPC ....... A61B 5/055; A61B 5/4244; A61B 6/032; A61B 8/485; A61B 8/0858; A61B 8/469; G01S 7/52042; G01S 7/52036; G01S 7/52071; G01S 7/52073; G16H 50/30
See application file for complete search history.

(56) References Cited

U.S. PATENT DOCUMENTS

| 2003/0233039 | A1 | 12/2003 | Shao et al. |
| 2006/0173319 | A1 | 8/2006 | Sumi |
| 2006/0247527 | A1 | 11/2006 | Maruyama |
| 2007/0238990 | A1* | 10/2007 | Haras ..................... A61B 6/465 |
| | | | 600/431 |

(Continued)

FOREIGN PATENT DOCUMENTS

| CN | 104545802 A | 4/2015 |
| JP | 2004-321582 A | 11/2004 |

(Continued)

OTHER PUBLICATIONS

International Search Report dated Mar. 19, 2019 in PCT/JP2018/047963 (with English translation), 5 pages.

(Continued)

*Primary Examiner* — Boniface Ngathi N
(74) *Attorney, Agent, or Firm* — Oblon, McClelland, Maier & Neustadt, L.L.P.

(57) ABSTRACT

An analysis apparatus includes processing circuitry configured to obtain quantitative values of a plurality of types of tissue properties relating to a region of interest of a subject, and generate a diagram of the region of interest based on the quantitative values.

26 Claims, 27 Drawing Sheets

(51) Int. Cl.
   *G01S 7/52* (2006.01)
   *A61B 6/00* (2006.01)
(52) U.S. Cl.
   CPC ......... *A61B 6/5217* (2013.01); *G01S 7/52042* (2013.01)

(56) References Cited

U.S. PATENT DOCUMENTS

2010/0331688 A1   12/2010   Baba
2012/0215101 A1   8/2012    Maleke et al.
2013/0208970 A1*  8/2013    Fujisawa ................ A61B 6/507
                                                      382/131

FOREIGN PATENT DOCUMENTS

| JP | 2005-92853 | 4/2005 |
|---|---|---|
| JP | 2005-528974 A | 9/2005 |
| JP | 2006-326285 A | 12/2006 |
| JP | 2011-10689 A | 1/2011 |
| JP | 2011-10775 | 1/2011 |
| JP | 2011-239813 A | 12/2011 |
| JP | 2012-170823 A | 9/2012 |
| JP | 2012-176289 A | 9/2012 |
| JP | 2015-37472 | 2/2015 |
| WO | WO 2017/068892 A1 | 4/2017 |

OTHER PUBLICATIONS

Combined Chinese Office Action and Search Report dated Jun. 25, 2021 in Chinese Patent Application No. 201880003837.8, 9 pages.
Zhi Zhang et al.; Operations Management; Dec. 1991; with English translation.
Office Action dated Jul. 21, 2022, issued in Chinese Patent Application No. 201880003837.8.

* cited by examiner

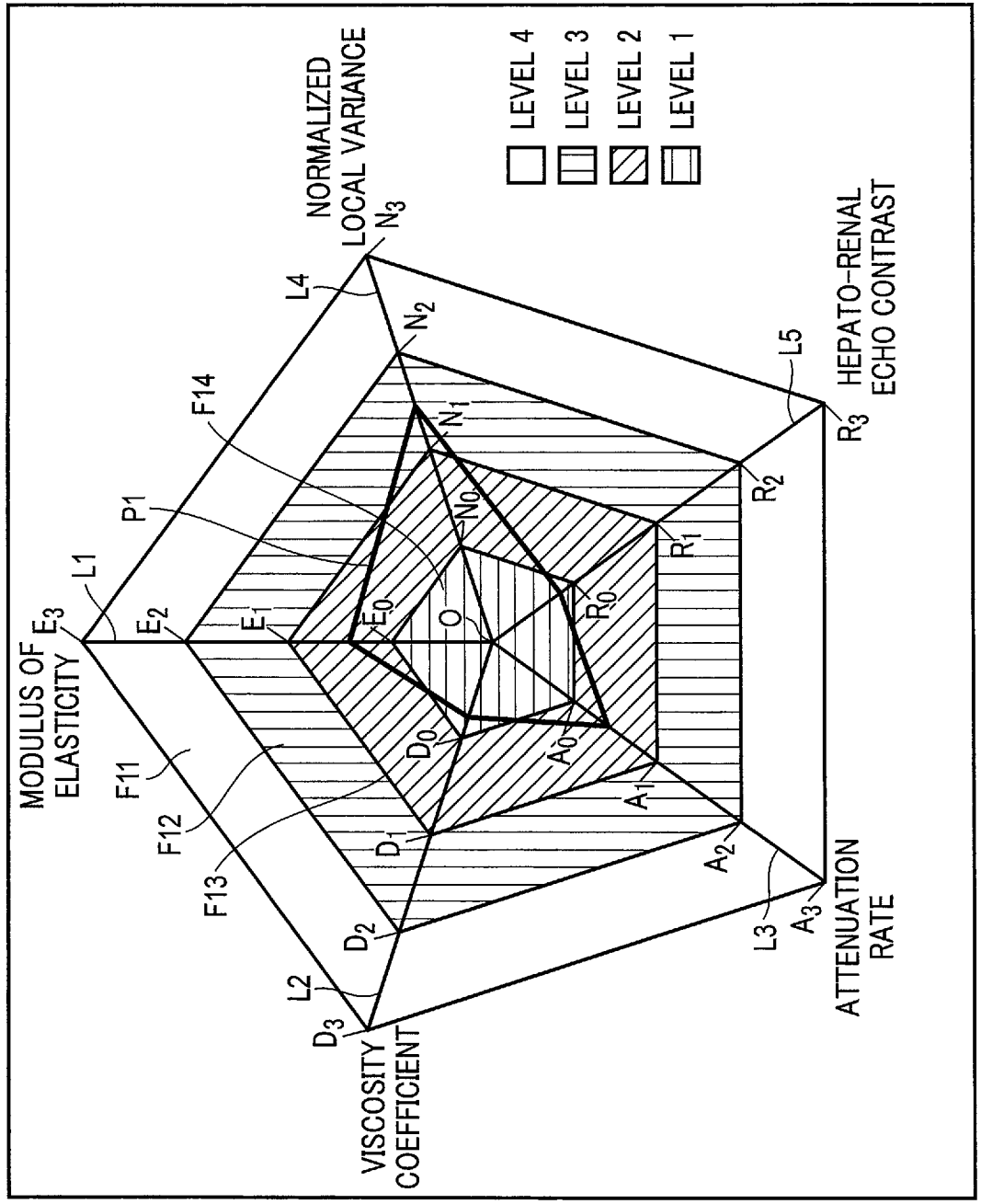
F I G. 7

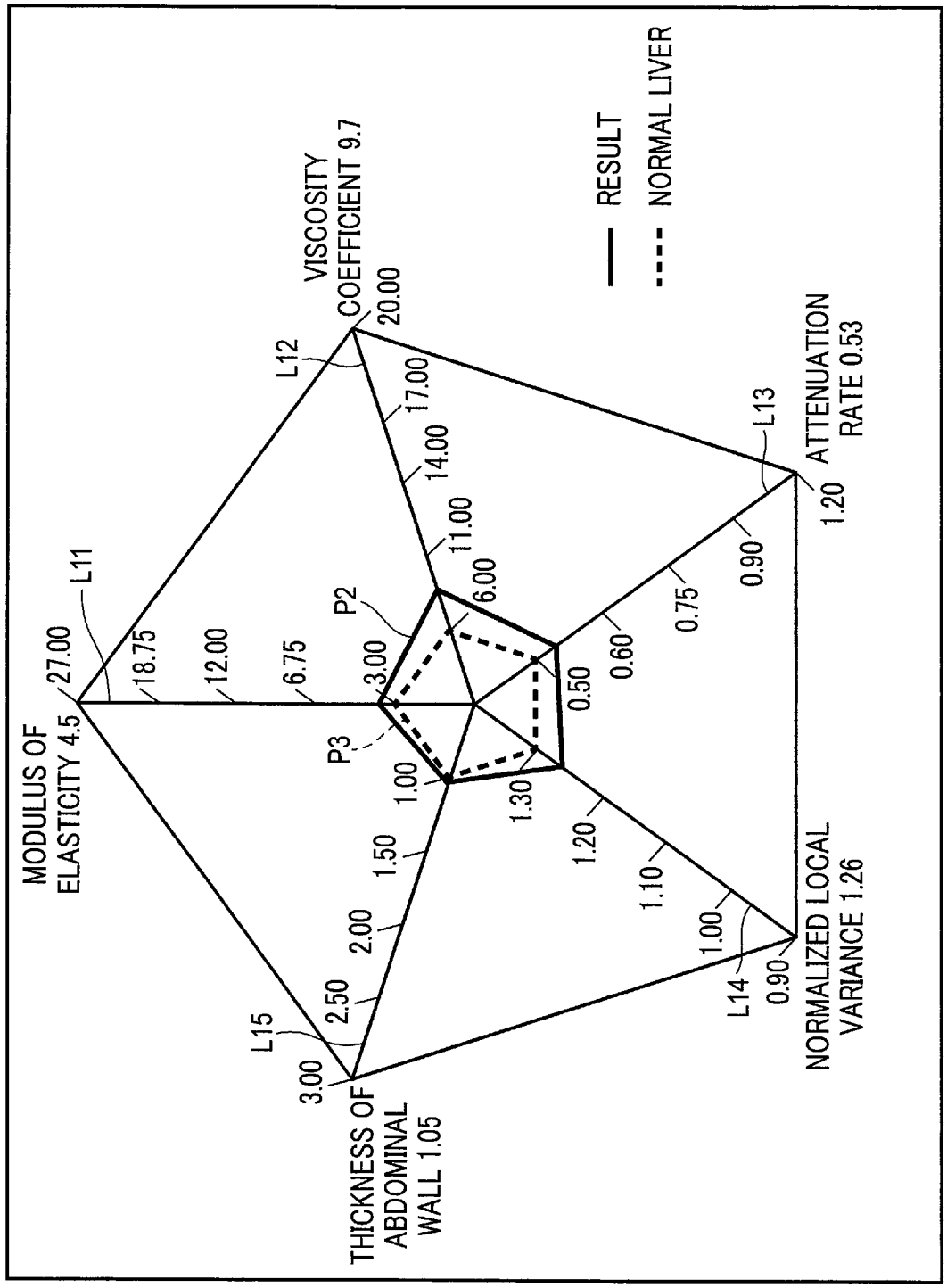
F I G. 14

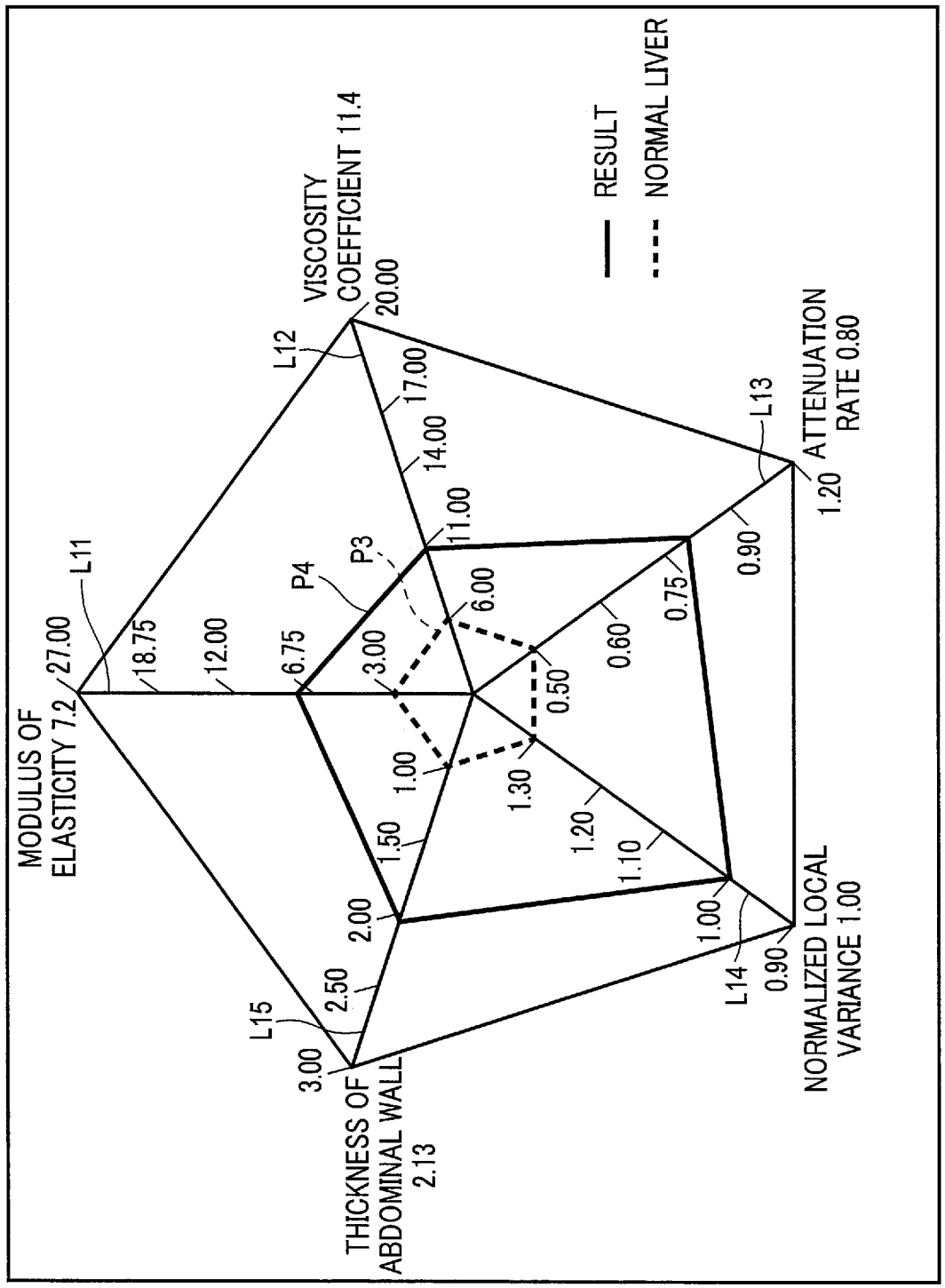
F I G. 15

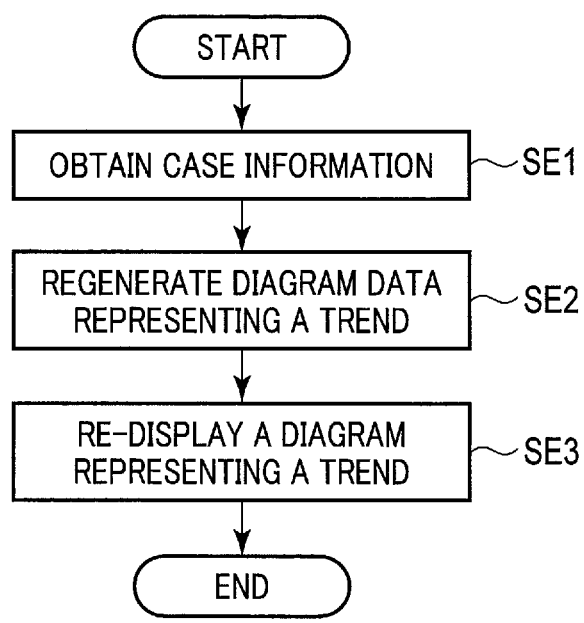
F I G. 19

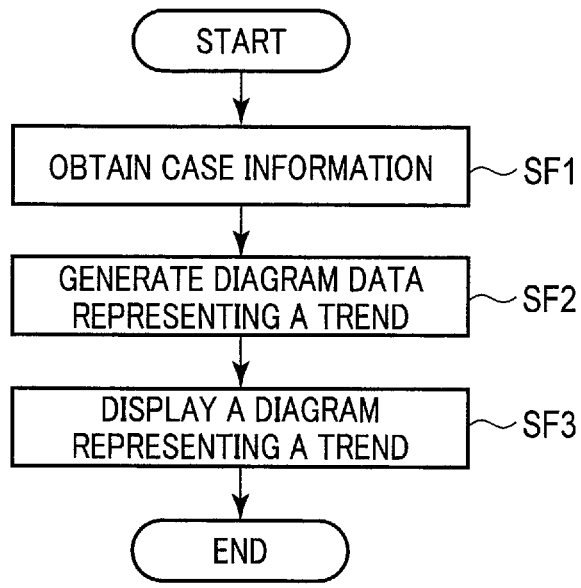
F I G. 21
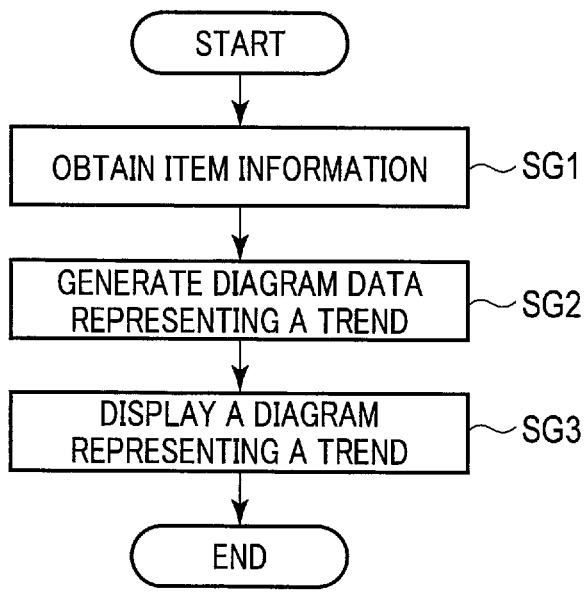
F I G. 22

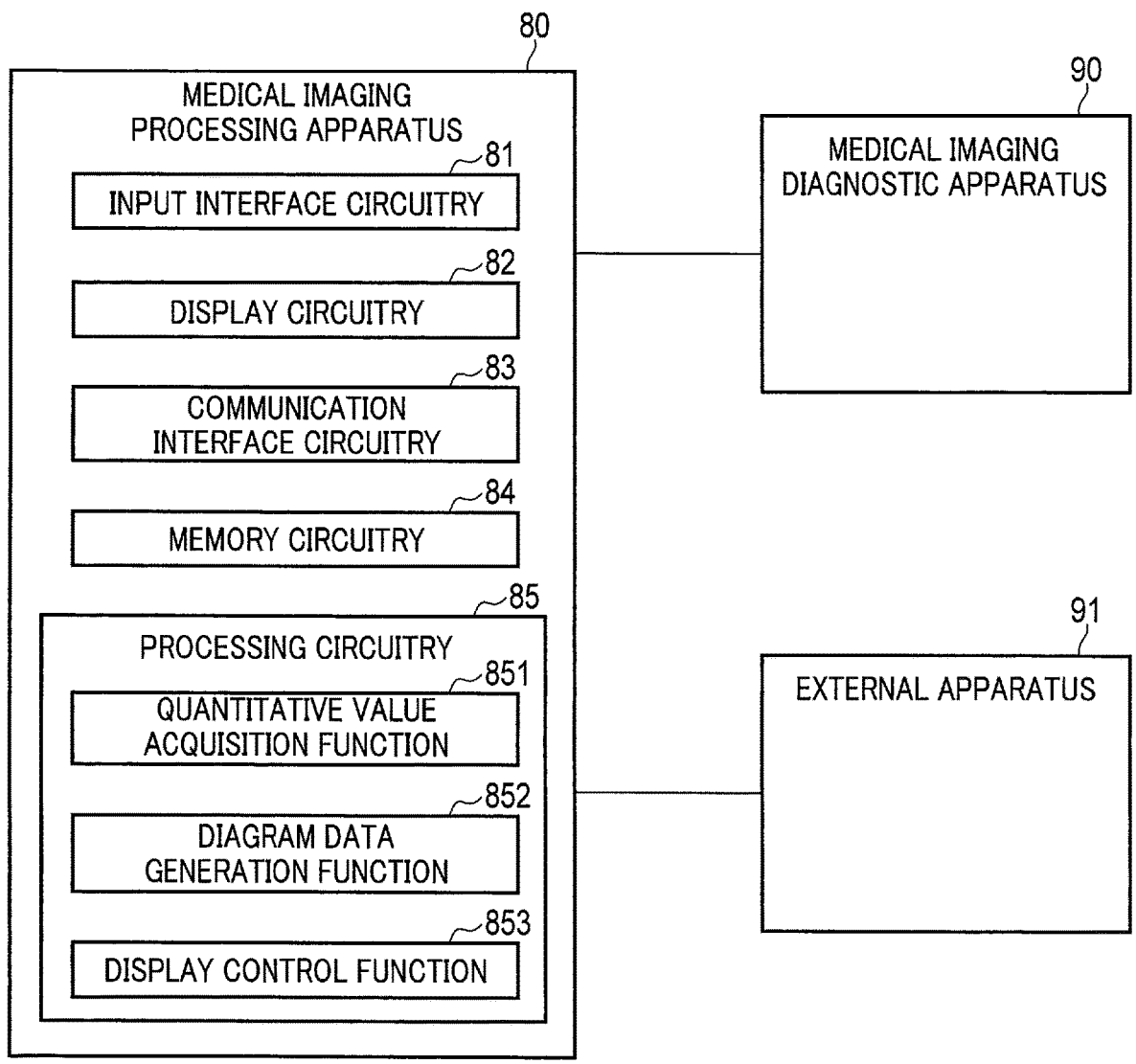
F I G. 25

ANALYSIS APPARATUS

CROSS-REFERENCE TO RELATED APPLICATIONS

This application is a Continuation Application of PCT Application No. PCT/JP2018/047963, filed Dec. 26, 2018 and based upon and claims the benefit of priority from the Japanese Patent Application No. 2017-252111, filed Dec. 27, 2017, the entire contents of all of which are incorporated herein by reference.

FIELD

Embodiments of the present invention relate to an analysis apparatus.

BACKGROUND

In recent years, an application for quantifying tissue properties of a subject with the use of a medical imaging diagnostic apparatus, such as an ultrasound diagnostic apparatus, a magnetic resonance imaging (MRI) apparatus, a computed tomography (CT) apparatus, etc., has been developed.

Quantitative values calculated by such an application are presented to a user in the form of image and/or numerical information, and utilized for diagnosis, etc.

Sometimes a single type of tissue property to be quantified is insufficient to conduct accurate diagnosis. For example, quantification of the stiffness of a liver by the use of an ultrasound diagnostic apparatus and subsequent presentation of an image and numerical information showing the stiffness of the liver to a user is already known; however, there is sometimes a case where identical stiffness is measured for both hepatitis and mild liver cirrhosis. In other words, mere quantification and presentation of a single type of tissue property sometimes fails to lead to identification of disease.

BRIEF DESCRIPTION OF THE DRAWINGS

FIG. 7 is a diagram showing an example of a radar chart displayed on the display device according to the first embodiment.

FIG. 14 is a diagram showing an example of a radar chart displayed on the display device according to the second modification.

FIG. 15 is a diagram showing an example of a radar chart displayed on the display device according to the second modification.

FIG. 19 of a flowchart showing an example of operations of the control circuitry performed when a display of a trend map based on empirical values is switched.

FIG. 21 is a flowchart showing an example of operations of the control circuitry performed when a diagram suitable for diagnosis of a suspected disease is generated.

FIG. 22 is a flowchart showing operations of the control circuitry performed when a diagram is generated by selecting items.

FIG. 25 is a block diagram showing a configuration of an analysis system according to the second embodiment.

DETAILED DESCRIPTION

Embodiments will be described below with reference to the drawings.

First Embodiment

An ultrasound diagnostic apparatus 1 according to the first embodiment will be described with reference to the block diagram shown in FIG. 1.

Figure 1:
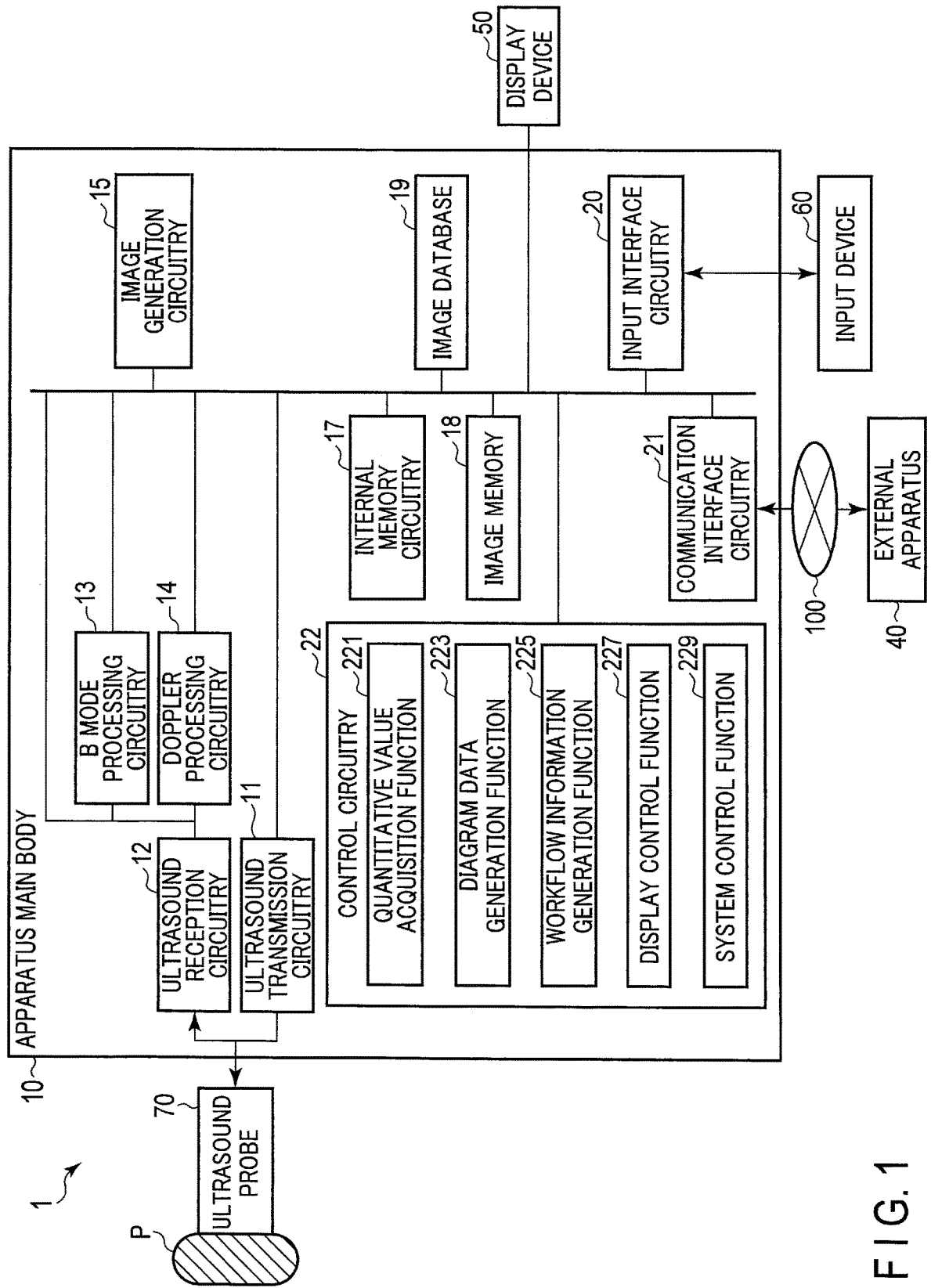
FIG. 1 is a diagram showing a configuration of an ultrasound diagnostic apparatus according to a first embodiment.

As shown in FIG. 1, the ultrasound diagnostic apparatus 1 comprises an apparatus main body 10, an ultrasound probe 70, a display device 50, and an input device 60. The apparatus main body 10 is connected to an external apparatus 40 via a network 100. The apparatus main body 10 is connected to the display device 50 and the input device 60.

The ultrasound probe 70 includes, for example, plurality of piezoelectric transducers, a matching layer provided in each piezoelectric transducer, and a backing material for preventing backward propagation of ultrasound from the piezoelectric transducers. The ultrasound probe 70 is detachably attached to the apparatus main body 10. The piezoelectric transducers generate ultrasound based on a drive signal supplied from ultrasound transmission circuitry 11 included in the apparatus main body 10. The ultrasound probe 70 may be provided with a button which is pressed when performing offset processing or freezing of ultrasound images, which will be described later.

When ultrasound is transmitted from the ultrasound probe 70 to a subject P, the transmitted ultrasound is reflected at an interface of media having different acoustic impedances in body tissue of the subject P, and the reflected wave (signal) is received at the piezoelectric transducers of the ultrasound probe 70. The amplitude of the received reflected wave signal depends on the difference in acoustic impedances of the discontinuous surfaces by which ultrasound is reflected. In a case where the transmitted ultrasound pulse is reflected by a moving object, such as flowing blood or a surface like a cardiac wall, a received signal of the transmitted ultrasound pulse is subjected to a frequency shift due to the Doppler effect, while depending on a velocity component of the moving object with respect to the direction of the transmitted ultrasound. The ultrasound probe 70 receives the reflected wave signal from the subject P, and converts it into an electrical signal.

The apparatus main body 10 shown in FIG. 1 is an apparatus that generates an ultrasound image based on the reflected wave signal received by the ultrasound probe 70. As shown in FIG. 1, the apparatus main body 10 includes ultrasound transmission circuitry 11, ultrasound reception circuitry 12, B-mode processing circuitry 13, Doppler processing circuitry 14, image generation circuitry 15, internal memory circuitry 17, an image memory 18 (cine memory), an image database 19, input interface circuitry 20, communication interface circuitry 21, and control circuitry 22.

The ultrasound transmission circuitry 11 is a processor that supplies a drive signal to the ultrasound probe 70. The ultrasound transmission circuitry 11 is implemented by, for example, a trigger generation circuit, a delay circuit, and a pulser circuit. The trigger generation circuit repeatedly generates rate pulses for formation of transmission at a predetermined rate frequency under control of the control circuitry 22. The delay circuit provides each rate pulse generated by the trigger generation circuit with a delay time for each piezoelectric transducer, which is necessary for converging ultrasound generated by the ultrasound probe 70 in a beam form and determining transmission directivity. The pulser circuit applies a drive signal (drive pulse) to the ultrasound probe 70 at times based on the rate pulse under the control of the processing circuitry 22. By varying the delay time provided to each rate pulse by the delay circuit, the transmission direction from the piezoelectric transducer surface can be freely adjusted.

The ultrasound reception circuity 12 is a processor that performs various processes on the reflected wave signal received by the ultrasound probe 70 to generate a reception signal. The ultrasound reception circuity 12 is realized by, for example, an amplifier circuit, an A/D converter, a reception delay circuit, and an adder. The amplifier circuit performs a gain-correction process by amplifying the reflected wave signal received by the ultrasound probe 70 for each channel. The A/D converter converts the gain-corrected reflected wave signal into a digital signal. The reception delay circuit provides the digital signal with a delay time necessary for determining reception directivity. The adder sums a plurality of digital signals each provided with a delay time. Through the summation process of the adder, a reception signal with an enhanced reflected component is generated in a direction corresponding to the reception directivity.

The B-mode processing circuity 13 is a processor that generates B-mode data based on the reception signal received from the ultrasound reception circuity 12 under the control of the control circuitry 22. The B-mode processing circuitry 13 performs an envelope detecting process, a logarithmic amplifying process, and the like, on, for example, the reception signal received from the ultrasound reception circuity 12 to generate data (B-mode data) that expresses signal intensity by brightness. The generated B-mode data is stored in a raw data memory (not shown) as B-mode raw data on an ultrasound scan line, which is two-dimensionally distributed.

The Doppler processing circuitry 14 is a processor that generates Doppler data based on the reception signal received from the ultrasound reception circuity 12. The Doppler processing circuitry 14 extracts a component corresponding to a moving object from the reception signal received from the ultrasound reception circuity 12, and calculates information about the moving body based on the extracted component for multiple points, thereby generating Doppler data. The moving object is for example blood flow or tissue. The information about the moving object includes a power of the component corresponding to the moving object, and an average and variance of a speed of the moving object, and the like. The generated Doppler data is stored in a raw data memory (not shown) as Doppler raw data on a two-dimensionally distributed ultrasound scan line.

The image generation circuitry 15 is a processor that is capable of generating various types of ultrasound image data, based on signals and data generated via the ultrasound reception circuity 12, the B-mode processing circuitry 13 and the Doppler processing circuitry 14. For example, the image generation circuitry 15 generates B-mode image data based on the B-mode raw data stored in the raw data memory. The B-mode image data has pixel values (brightness values) reflecting, for example, characteristics of the ultrasound probe, such as sound convergence, and sound-field characteristics of an ultrasound beam (e.g., a transmitted/received beam). For example, B-mode image data has relatively higher brightness in the vicinity of the focus of ultrasound in the scanned area than in the unfocused part. The image generation circuitry 15 generates Doppler image data relating to, for example, an image showing a distribution of an average speed of the moving object, an image showing a dispersion of a speed of the moving object, and an image showing a power of the component corresponding to the moving object.

The image generation circuitry 15 generates ultrasound image data for display by, for example, a coordinate conversion process. The coordinate conversion process is a process for converting, for example, signal sequences of scanning lines of ultrasound scanning, which is constituted by B-mode data and Doppler data, into video signals which take the form of scanning line signal sequences in a common video format typified by, for example, a television format.

The image generation circuitry 15 generates ultrasound image data showing information related to tissue properties of a subject P. Tissue properties are, for example, properties or a state of tissue. The tissue property image data is, for example, elasticity image data relating to an image showing elasticity (stiffness) of tissue, viscosity image data related to an image showing viscosity of tissue, attenuation image data related to an image showing a degree of attenuation of ultrasound propagating in tissue of a subject P, and dispersion image data related to an image showing a degree of dispersion of signals reflected in the inside of tissue of a subject P.

The elasticity image data is obtained by quantifying stiffness of tissue, for example. When a push pulse having high acoustic radiation force is transmitted from the ultrasound probe 70, tissue is partially deformed and a shear wave is generated. The elasticity image data is generated by observing how the generated shear wave propagates, through transmission and reception of a tracking pulse. Specifically, a reception signal or Doppler data, which is generated by transmitting and receiving a tracking pulse, is processed to calculate a change in displacement over time for each location in the region of interest to be imaged, and a propagation speed of a shear wave is then calculated based on the change in displacement over time to generate elasticity image data. A quantitative value of elasticity is not limited to a modulus of elasticity. For example, a propagation speed itself may be a quantitative value of the elasticity. The elasticity image data may be generated based on a change (strain) caused in a shape of tissue due to a dynamic load being applied to tissue of a subject.

The viscosity image data is obtained by quantifying viscosity of tissue, for example. The viscosity image data is generated based on, for example, a frequency and a propagation speed of a shear wave. A quantitative value of a viscosity is not limited to a viscosity coefficient. For example, a gradient in a distribution of a frequency and a propagation speed, and the like, may also be a quantitative value of viscosity. The viscosity image data is generated by processing the reception signal or Doppler data generated by transmission/reception of a tracking pulse, similar to the elasticity image data, for example.

The attenuation image data is obtained by quantifying a degree of ultrasound attenuation in a subject's tissue, for example. The attenuation image data is generated by processing, for example, the reception signal generated by the ultrasound reception circuitry 12, the B-mode data generated by the B-mode processing circuitry 13, or the B-mode image data generated by the image generation circuitry 15. Specifically, the attenuation image data is generated by, for example, transmitting and receiving an ultrasound pulse of a narrow bandwidth, reducing influence related to gain-correction or sound field, etc. in the obtained reception signal, B-mode data, or B-mode image data, and calculating an amount of change in a depth direction of signal intensity. In addition, the attenuation image data is generated by, for example, transmitting and receiving a plurality of ultrasound pulses having different center frequencies to obtain reception signals and to compare a degree of change in intensity of each of the obtained reception signals with respect to a depth direction, and then estimating an amount of attenuation unique to a subject.

The dispersion image data is obtained by quantifying a degree of dispersion of signals reflected in the inside of tissue of a subject P, for example. The dispersion image data is generated by processing, for example, the reception signal generated by the ultrasound reception circuitry 12, the B-mode data generated by the B-mode processing circuitry 13, or the B-mode image data generated by the image generation circuitry 15.

Specifically, the dispersion image data is generated by, for example, locally calculating a degree of deviation from a Rayleigh distribution of a signal amplitude distribution of the reception signal generated via the ultrasound reception circuitry 12 for each local area.

Each of the generated elasticity image data, viscosity image data, attenuation image data, and dispersion image data is associated with pixel values corresponding to a predetermined color in accordance with a quantitative value of tissue properties (a tissue property parameter) calculated for each pixel. The generated elasticity image data, viscosity image data, attenuation image data, and dispersion image data are displayed on the display device 50 as color maps.

The generated B-mode image data, Doppler image data, elasticity image data, viscosity image data, attenuation image data, and dispersion image data are converted into a format in conformity with a standard, for example DICOM (digital imaging and communication in medicine), and are stored in the image database 19, for example.

As the display device 50, for example, a cathode-ray tube (CRT) display, a liquid crystal display, an organic electroluminescence (EL) display, an LED display, a plasma display, or any other display known in the relevant technical field may be used as appropriate. The display device 50 may be a touch panel having an input function with which a touch operation is performed.

The internal memory circuitry 17 includes, for example, a magnetic or optical storage medium, or a processor-readable storage medium such as a semiconductor memory. The internal memory circuitry 17 stores, for example, a control program for realizing ultrasound transmission and reception, a control program for performing image processing, and a control program for performing display processing. The internal memory circuitry 17 also stores a control program for realizing various functions according to the present embodiment. The internal memory circuitry 17 also stores diagnostic information (such as a patient's ID, and a doctor's findings), a diagnostic protocol, a body mark generation program, and a data group such as a conversion table in which the range of color data used for imaging is preset for each diagnostic site. The internal memory circuitry 17 may store anatomical illustrations, for example, an atlas, relating to the structures of internal organs in the body.

The internal memory circuitry 17 stores various image data generated at the image generation circuitry 15, in accordance with a memory operation that is input via the input interface circuitry 20. The internal memory circuitry 17 may store various image data generated at the image generation circuitry 15 together with the operation order and operation time, in accordance with a memory operation that is input via the input interface circuitry 20. The internal memory circuitry 17 can transfer the stored data to an external device via the communication interface circuitry 21.

The internal memory circuitry 17 stores a plurality of thresholds for each type of tissue properties in advance. A tissue property parameter is a quantitative value of tissue properties, and is, for example, an index value indicating stiffness of tissue, an index value indicating viscosity of tissue, an index value indicating a degree of attenuation of ultrasound in subject tissue, a ratio of reflection intensity of ultrasound in a liver and a kidney, a degree of dispersion of signals reflected in the inside of tissue of a subject P, and a strain ratio indicating a ratio of stiffness of tissue in a region of interest to stiffness of tissue at a predetermined location, which serves as a reference point. The plurality of thresholds are used so that a user can know the stage at which each tissue parameter is. A stage is referred to as an index indicating a degree of progression of a particular disease case, for example. A stage does not necessarily show only a degree of progression of a particular disease case; a stage may indicate a degree of progression of multiple diseases case.

The index value indicating stiffness of tissue is a quantitative value used when diagnosis of hepatic fibrosis is conducted, for example. The index value indicating stiffness of tissue is for example a modulus of elasticity. A modulus of elasticity becomes greater as hepatic fibrosis progresses, for example. The index value indicating stiffness of tissue can be obtained by analyzing elasticity image data, for example.

The index value indicating viscosity of tissue is a quantitative value used when diagnosis of a case in which viscosity is significantly increased due to necrosis or inflammation, for example acute hepatitis, is conducted. The index value indicating viscosity of tissue may be expressed by a viscosity coefficient, for example. A viscosity coefficient becomes greater when a patient suffers from, for example, acute hepatitis. The index value indicating a viscosity of tissue is obtained by analyzing viscosity image data, for example.

The index value indicating a degree of attenuation of ultrasound in subject tissue is a quantitative value used when a diagnosis of a fatty liver is conducted, for example. The index value indicating a degree of attenuation of ultrasound in subject tissue may be expressed by, for example, an attenuation rate. An attenuation rate becomes greater when a patient suffers from, for example, fatty liver. The index value indicating a degree of attenuation of ultrasound in subject tissue is obtained by analyzing attenuation image data, for example.

A ratio of reflection intensity of ultrasound in a liver and a kidney is a quantitative value used when a diagnosis of a fatty liver is conducted, for example. The ratio of intensity of ultrasound reflection in a liver and a kidney is obtained as a measurement item relating to a liver function, as a kidney is located in the proximity of a liver. The ratio of intensity of ultrasound reflection in a liver and a kidney is expressed by a hepato-renal echo contrast, using a kidney as a reference, for example. If a hepato-renal echo contrast is high, in other words, echo intensity of a liver is higher than echo intensity of a kidney, a fatty liver is suspected. The ratio of intensity of ultrasound reflection in a liver and a kidney is obtained by, for example, analysis of B-mode image data.

A degree of dispersion of signals reflected in the inside of tissue of a subject P is a quantitative value used when a diagnosis of a fatty liver is conducted for example. A degree of dispersion of intensity of signals reflected in the inside of tissue of a subject P is expressed by a normalized local variance (NLV), for example. An NLV indicates a degree of agreement between a probability density distribution of brightness values of echo signals reflected by a liver and a Rayleigh distribution, for example. To observe a liver which is suspected to be a fatty liver, as a ratio of fat in the liver increases, a B-mode image becomes uniform, like a phantom, and a probability density distribution of amplitude values, which indicate intensity of echo signals reflected in the liver, becomes similar to a Rayleigh distribution. In this case, an NLV becomes close to 1. To observe a liver which is suspected to be a liver fibrosis, as the liver fibrosis progresses, the probability density distribution of amplitude values, which indicate intensity of echo signals reflected in the liver, comes to reflect a structure suffering from fibrosis, and to deviate from the Rayleigh distribution. In this case, an NLV becomes higher (becomes further away from 1). A degree of dispersion of signals reflected in the inside of tissue of a subject P is obtained by analyzing, for example, dispersion image data.

A strain ratio is a quantitative value used when diagnosis of hepatic fibrosis is conducted, for example. A strain ratio is a ratio between a modulus of elasticity of an ROI and a predetermined modulus of elasticity as a reference. A strain ratio becomes greater as hepatic fibrosis progresses, for example. A strain ratio is obtained by analyzing, for example, elasticity image data.

A plurality of thresholds may be set or changed by an operator, etc. via the input interface circuitry 20. A plurality of thresholds may be stored for each type of tissue properties as a set of thresholds including at least two thresholds. In this case, an operator can select a threshold set as appropriate from the stored threshold sets. Tissue properties for which thresholds are to be set may be set or changed by an operator, etc. via the input interface circuitry 20.

The image memory 18 includes, for example, a magnetic or optical storage medium, or a processor-readable storage medium such as a semiconductor memory. The image memory 18 stores image data pieces corresponding to a plurality of frames immediately before a freeze operation that is input through the input interface circuitry 20. The image data stored in the image memory 18 is, for example, continuously displayed (cine-displayed).

The image database 19 stores image data transferred from the external device 40. For example, the image database 19 obtains, from the external apparatus 40, and then stores historical image data concerning the same patient obtained from the past medical examination. The historical image data includes ultrasound image data, computed tomography (CT) image data, MR image data, positron emission tomography (PET)-CT image data, PET-MR image data, and X-ray image data. The historical image data is stored as, for example, three-dimensional volume data and rendering image data.

The image database 19 may store desired image data by reading image data stored in a storage medium such as an MO, a CD-R, or a DVD.

The input interface circuitry 20 receives various instructions from an operator through the input device 60. The input device 60 is, for example, a mouse, a keyboard, a panel switch, a slider switch, a trackball, a rotary switch, a touch panel, or a touch command screen (TCS). The input interface 20 is connected to the control circuitry 22 via, for example, a bus, generates electrical signal in response to an operation instruction that is input by the operator, and outputs the electrical signal to the control circuitry 22. In the embodiments described herein, the input interface circuitry 20 is not limited to circuitry connected to physical operation components such as a mouse, a keyboard, etc. The input interface circuitry 20 may include processing circuitry of electric signals which receives, as radio signals from the ultrasound diagnosis apparatus 1, electric signals corresponding to an operation instruction input from an external input device independently provided, and outputs the electric signals to the control circuitry 22.

The communication interface circuitry 21 is connected to the external apparatus 40 via, for example, the network 100, and performs data communication with the external apparatus 40. The external apparatus 40 is, for example, a database of a picture archiving and communication system (PACS), which is a system that manages data of various medical images, and a database of an electronic medical record system which manages electronic medical records accompanied with medical images. The external apparatus 40 is a medical imaging diagnostic apparatus other than the ultrasound diagnostic apparatus 1 according to the present embodiment, such as an X-ray CT apparatus, an MRI apparatus, a nuclear medicine diagnostic apparatus, or an X-ray diagnostic apparatus. The standard of the communication with the external apparatus 40 may be any standard, for example DICOM.

The control circuitry 22 is a processor acting as a nerve center of the ultrasound diagnostic apparatus 1, for example. The control circuitry 22 executes the operating program stored in the internal memory circuitry 17 to realize a function corresponding to the operating program. Specifically, the control circuitry 22 includes a quantitative value acquisition function 221, a diagram data generation function 223, a workflow information generation function 225, a display control function 227, and a system control function 229.

The quantitative value acquisition function 221 is a function of acquiring tissue property parameters of a region of interest of a subject P. When the quantitative value acquisition function 221 is executed, the control circuitry 22 analyzes B-mode image data, elasticity image data, viscosity image data, attenuation image data, or dispersion image data, and acquires a predetermined tissue property parameter.

The diagram data generation function 223 is a function of generating a diagram of a region of interest based on a plurality of quantitative values obtained by the quantitative value acquisition function 221. When the diagram data generation function 223 is executed, the control circuitry 22 generates diagram data presenting content of a diagram displayed as diagnosis support information relating to the region of interest, by using quantitative values for each type of tissue properties obtained from the region of interest of the subject P, and thresholds prepared for each of the quantitative values. The diagram includes a radar, a flowchart, a bar chart, and a line graph, etc.

The workflow information generation function 225 is a function of generating workflow information based on information that determines a plurality of tissue property types necessary for a predetermined tissue characterization. The workflow information is information which supports a tissue characterization. Workflow information includes the procedure for acquiring tissue property parameters, and various setting information, etc. When the workflow information generation function 225 is executed, the control circuitry 22 retrieves information to specify a plurality of tissue property types necessary for a predetermined tissue characterization, from, for example, the internal memory circuitry 17. The control circuitry 22 generates workflow information for acquiring a plurality of tissue property parameters based on the retrieved information.

The display control function 227 is a function which displays a diagram generated by the diagram data generation function 223 and workflow information generated by the workflow information generation function 225, and the like. If the display control function 227 is executed, the control circuitry 22 causes the display device 50 to display the workflow information. The control circuitry 22 causes the display device 50 to display a diagram. The control circuitry 22 may generate a user interface e.g., graphical user interface (GUI), through which an operator (for example, a surgeon) inputs various instructions by the input interface circuitry 20, and causes the display device 50 to display the generated GUI.

The system control function 229 is a function of controlling basic operations, such as the input and output, relative to the ultrasound diagnostic apparatus 1. When the system control function 229 is executed, the control circuitry 22 accepts an instruction to start activating a report generation application and acquiring tissue property parameters, via the input interface circuitry 20 for example. The inputs for activating the report generation application and acquiring tissue property parameters may be a single input.

Next, the operations of the ultrasound diagnostic apparatus 1 according to the first embodiment will be explained with reference to FIGS. 2 to 8.

Figure 2:
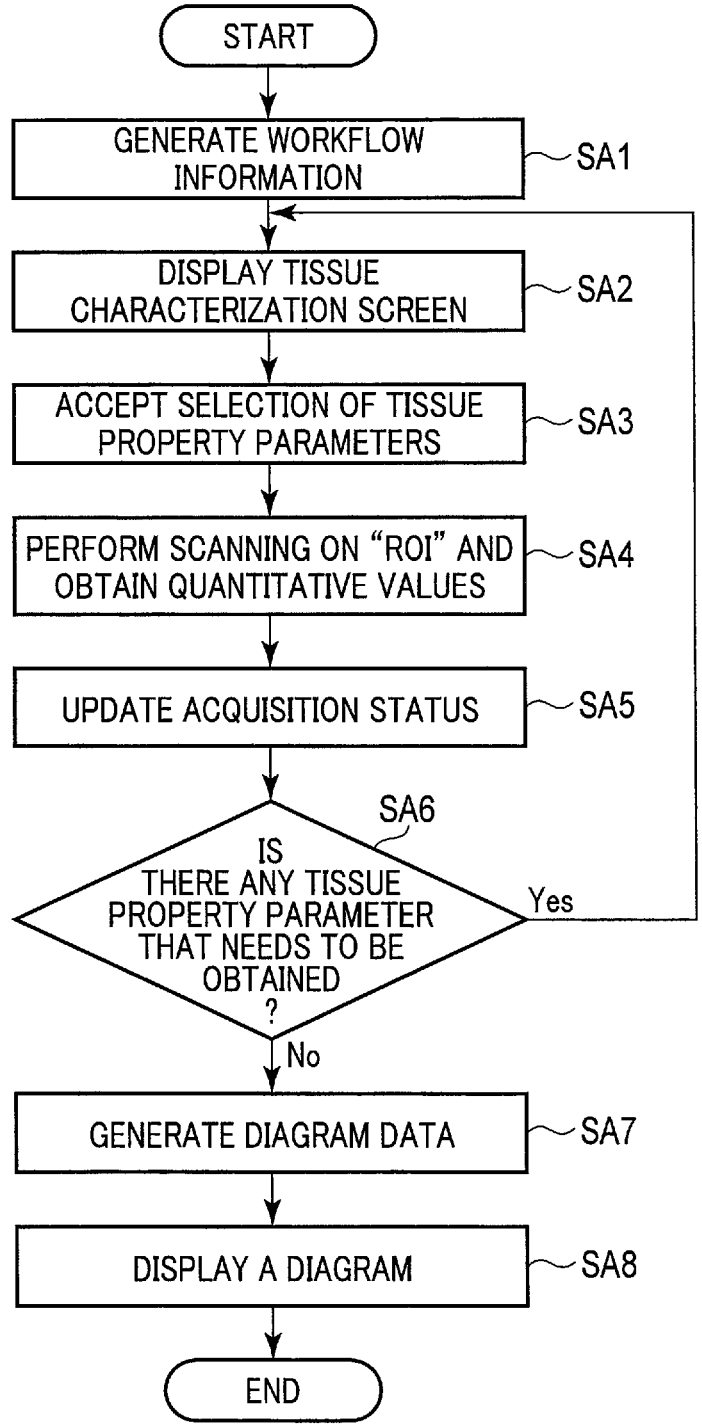
FIG. 2 is a flowchart showing operations of control circuitry performed when the ultrasound diagnostic apparatus according to the first embodiment generates a diagram related to a tissue characterization.

FIG. 2 is a flowchart showing an example of the operations of the control circuitry 22 performed when the ultrasound diagnostic apparatus 1 generates a diagram related to a tissue characterization according to the first embodiment. In the following description, let us suppose that ultrasound scanning is performed in a B-mode on a portion targeted for the tissue characterization in advance of performing the tissue characterization, and a B-mode image data is generated. Let us further suppose that the portion targeted to the tissue characterization is a liver. The diagram is, for example, a radar chart. Also, let us suppose that the tissue property parameters corresponding to the contents (items) of the radar chart are a modulus of elasticity, a viscosity coefficient, an attenuation rate, a normalized local variance, and a hepato-renal echo contrast.

When an instruction to conduct a tissue characterization for a liver, for example, is input via the input interface circuitry 20, the control circuitry 22 executes the workflow information generation function 225 and generates workflow information indicating acquisition procedure for acquiring a tissue property parameter for each tissue property type (step SA1). The workflow information may be stored in advance in the internal memory circuitry 17 for each tissue property type, for example. In this case, when a portion targeted for diagnosis is specified via the input interface circuitry 20, for example, the workflow information is combined as appropriate in accordance with the specified target portion and is retrieved from the internal memory circuitry 17. Alternatively, the workflow information may be stored in advance, in combination with a workflow for acquiring various tissue property parameters, in the internal memory circuitry 17. The workflow information includes, for example, conditions for ultrasound transmission, conditions for adjustment after receiving ultrasound, a type of image data to be obtained, the number of times image data is acquired per quantitative value acquisition, a method of calculating a representative value calculated for each shot (acquisition of image data), and a method of calculating a representative value of tissue property parameters used to generate a diagram, etc.

Conditions for ultrasound transmission are, for example, an amplitude, a frequency, a phase, and transmission timing of ultrasound to be transmitted. Conditions for adjustment after receiving ultrasound are, for example, conditions relating to image processing, such as gain, sensitivity time control (STC), dynamic range, frequency filters, and echo enhancement, etc., and conditions relating to a Doppler low cut filter, etc. A type of image data to be acquired is, for example, B-mode image data, elasticity image data, viscosity image data, attenuation image data, or dispersion image data, etc. The number of times image data is acquired per quantitative value acquisition is, for example, five times. The method of calculating a representative value calculated for each shot is for example a method of calculating a mean or a center value of tissue property parameters obtained for a region of interest (ROI) of a subject P. The method of calculating a representative value of tissue property parameters used when a diagram is generated is, for example, a method of calculating a mean or a median of all the representative values calculated (one for each shot).

Figure 3:
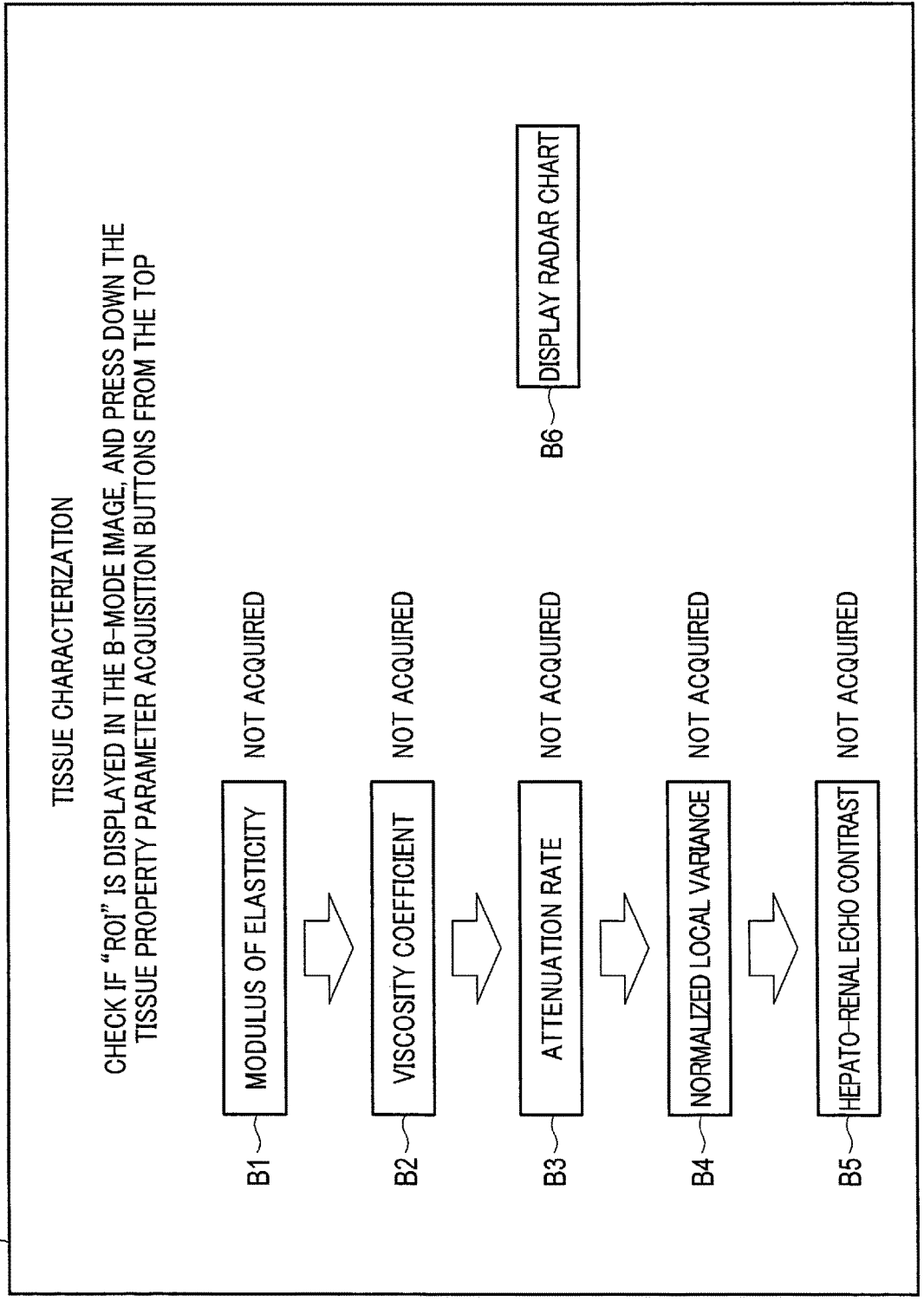
FIG. 3 is a diagram showing workflow information displayed on a display device according to the first embodiment.

Next, the control circuitry 22 executes the display control function 227, and displays, for example, a tissue characterization support screen (step SA2). FIG. 3 is a diagram showing an example of workflow information displayed on the display device 50 according to the first embodiment. FIG. 3 shows the tissue characterization support screen that guides an operator to obtain the tissue property parameters and displays a radar chart used for a tissue characterization.

The tissue characterization support screen shown in FIG. 3 displays a message: "Check if an ROI is displayed in the B-mode image, and press down the tissue property parameters acquisition buttons from the top". At this time, a user looks at the B-mode image, which is displayed in a window separate from the tissue characterization support screen, or on a separate monitor, to check if an ROI is displayed in the B-mode image. The tissue characterization support screen shown in FIG. 3 displays buttons B1, B2, B3, B4, an B5 that are capable of acquiring tissue property parameters required for generating radar chart data used for the tissue characterization. It is thereby possible for the operator to obtain quantitative values of tissue properties, namely a modulus of elasticity, a viscosity coefficient, an attenuation rate, a normalized local variance, and a hepato-renal echo contrast, in this order.

The tissue characterization support screen shown in FIG. 3 displays a button B6 for displaying a radar chart based on generated radar chart data.

Furthermore, the tissue characterization support screen shown in FIG. 3 displays an acquisition status indicating whether each tissue property parameter is acquired or not yet acquired. According to FIG. 3, in the initial state, each of a modulus of elasticity, a viscosity coefficient, an attenuation rate, a normalized local variance, and a hepato-renal echo contrast is displayed under the status of "not acquired yet". The status "not acquired yet" indicates that the tissue property parameter has not yet been acquired. The acquisition status is updated to "acquired" when a tissue property parameter under the status of "not acquired yet" is acquired. The acquisition status is stored in a predetermined memory implemented in, for example, the control circuitry 22.

After displaying the tissue characterization support screen, the control circuitry 22 accepts a selection of tissue properties for which a quantitative value is to be acquired (step SA3). At this time, in FIG. 3, let us suppose that the tissue property parameters are selected in the order of buttons B1, B2, B3, B4, and B5.

Figure 4:
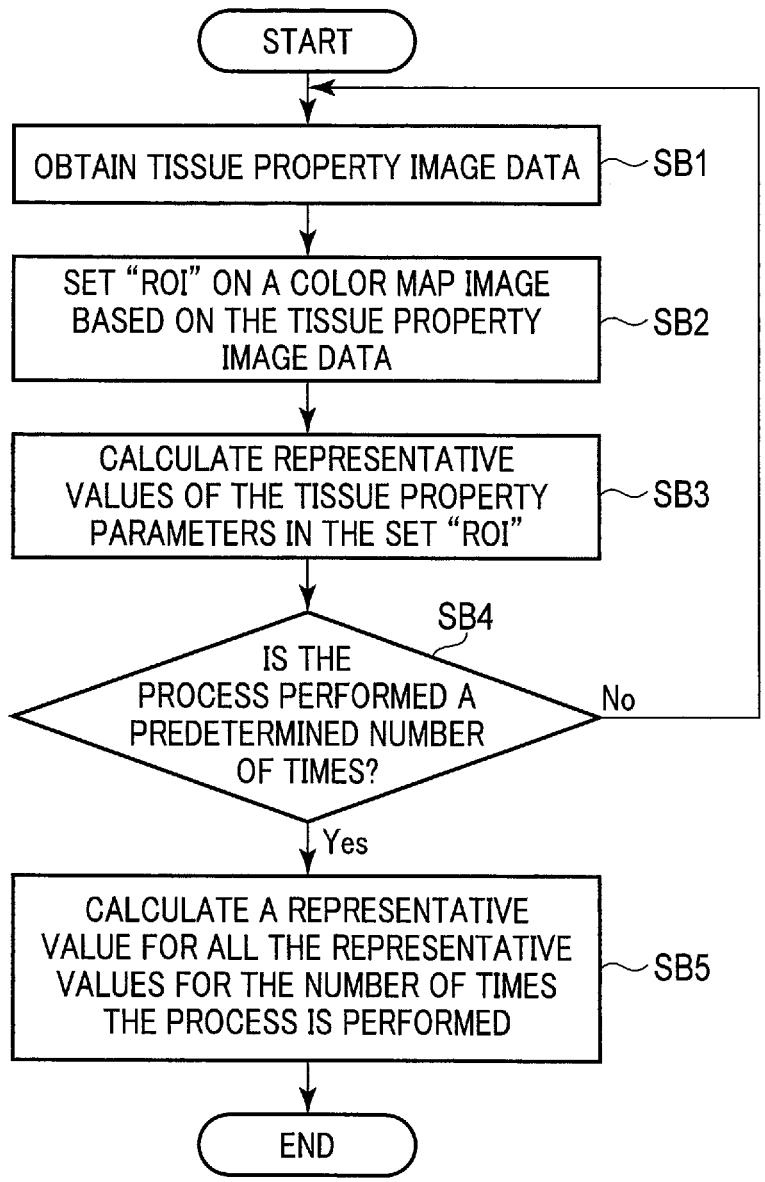
FIG. 4 is a flowchart showing operations of the control circuitry performed when the ultrasound diagnostic apparatus according to the first embodiment obtains quantitative values of tissue properties.

If button B1 is specified in step SA3, the control circuitry 22 obtains a modulus of elasticity based on workflow information used for obtaining a modulus of elasticity (step SA4). FIG. 4 is a flowchart showing an example of the operations of the control circuitry 22 performed when the ultrasound diagnostic apparatus according to the first embodiment obtains a tissue property parameter. In the following, a case where a modulus of elasticity is obtained will be explained as an example.

As shown in FIG. 4, the control circuitry 22 controls the ultrasound transmission circuitry 11, ultrasound reception circuitry 12, the Doppler processing circuitry 14, and the image generation circuitry 15, based on the workflow information used for obtaining a modulus of elasticity to generate elasticity image data (step SB1). For example, the ultrasound circuitry 11 causes the ultrasound probe 70 to transmit a push pulse under the control of the control circuitry 22. The ultrasound transmission circuitry 11 and the ultrasound reception circuitry 12 then cause the ultrasound probe 70 to transmit and receive a tracking pulse under the control of the control circuitry 22. The Doppler processing circuitry 14 then generates Doppler data based on a reception signal generated by the ultrasound reception circuitry 12 upon the transmission and reception of the tracking pulse under the control of the control circuitry 22. The image generation circuitry 15 calculates, under the control of the control circuitry 22, a change in displacement over time for each location in a region targeted for imaging, calculates a propagation speed of a shear wave for each location in the region targeted for imaging based on the change in displacement over time, and calculates a modulus of elasticity for each location in the region targeted for imaging based on the propagation speed, thereby generating elasticity image data.

The control circuitry 22 sets a predetermined region of interest on a color map image based on the generated elasticity image data (step SB2).

The control circuitry 22 calculates a representative value, for example a mean, of a modulus of elasticity of the region of interest, which is set in the previous step (step SB3). The control circuitry 22 determines whether or not the processing from step SB1 through step SB3 is performed a predetermined number of times, for example, five times (step SB4).

If it is determined that the processing from step SB1 through step SB3 is not performed the predetermined number of times (No in step SB4), the control circuitry 22 repeats the processing from step SB1 through step SB3 until the processing is performed the predetermined number of times. If it is determined that the processing from step SB1 through step SB3 is performed the predetermined number of times (Yes in step SB4), the control circuitry 22 calculates a representative value of the calculated representative values of the predetermined number of times, for example five times (step SB5). Through this process, a modulus of elasticity is obtained. The region of interest in step SB2 may be manually set via the input interface circuitry 20.

Returning to FIG. 2, when the modulus of elasticity is obtained in step SA4 shown in FIG. 2, the control circuitry 22 updates the acquisition status of the modulus of elasticity from "not yet acquired" to "acquired" in the predetermined memory which is controlled by the control circuitry 22 (step SA5). The tissue property parameters obtained in step SA4, such as the modulus of elasticity, may be stored in the internal memory circuitry 17.

The control circuitry 22 determines whether or not there are other tissue property types for which a quantitative value needs to be acquired (step SA6).

Figure 5:
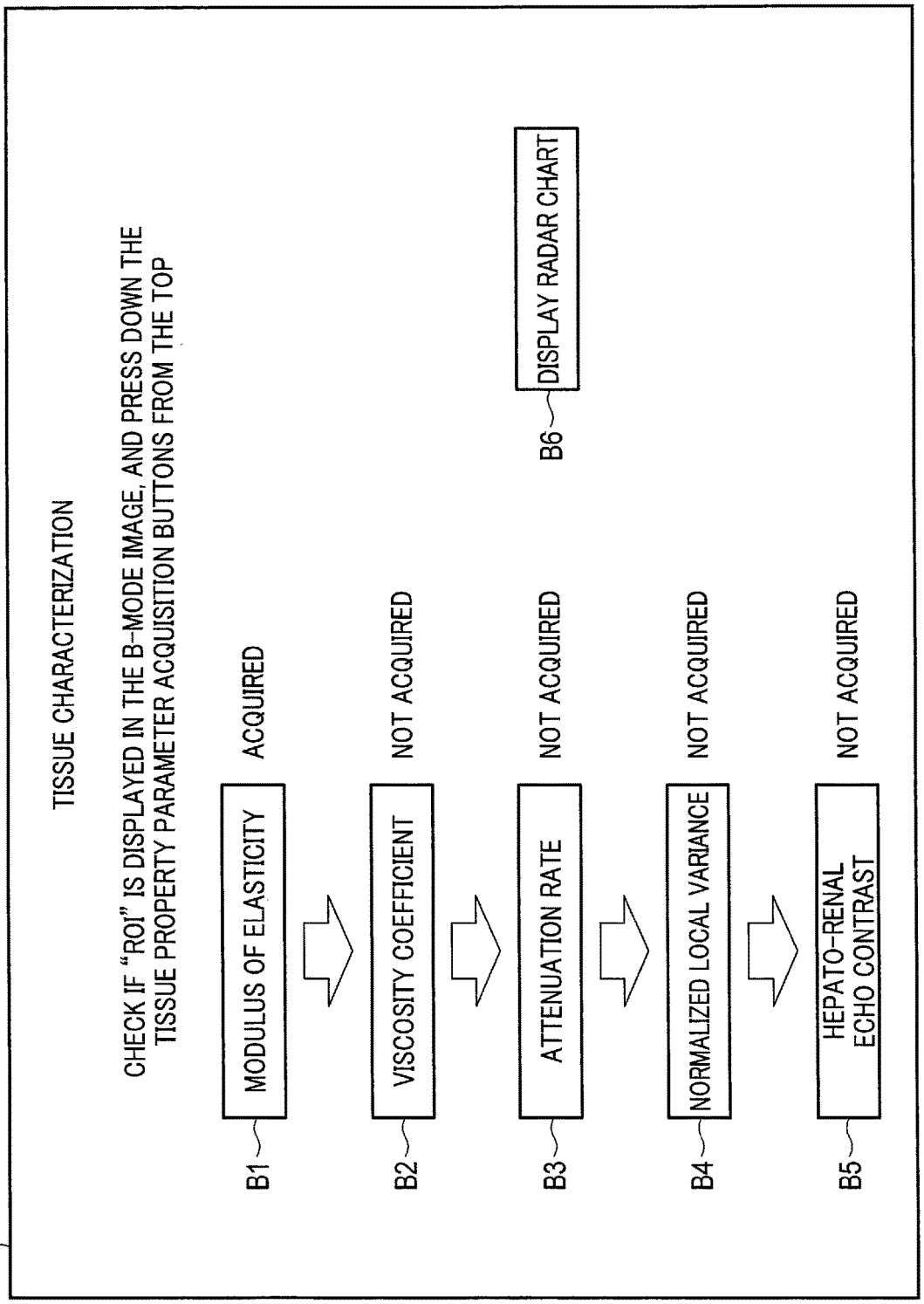
FIG. 5 is a diagram showing an updated tissue characterization support screen displayed on a display device according to the first embodiment.

If it is determined that there are other tissue property types for which a quantitative value needs to be acquired (Yes in step SA6), the control circuitry 22 executes the display control function 227 and reflects the updated acquisition status to the tissue characterization support screen shown in FIG. 3, and displays the tissue characterization support screen again (step SA2). FIG. 5 is a diagram showing an example of the updated tissue characterization support screen displayed on the display device 50 according to the first embodiment. According to FIG. 5, the acquisition status of the modulus of elasticity is shown as "acquired", after being updated.

After displaying the updated tissue characterization support screen as shown in FIG. 5, the control circuitry 22 accepts a selection of tissue properties for which quantitative values are to be acquired (step SA3).

If button B2 is specified in step SA3, the control circuitry 22 performs measurement based on the workflow information for obtaining a viscosity coefficient, and obtains a viscosity coefficient (step SA4). The operations of the control circuitry 22 and related circuitry when a viscosity coefficient is obtained are the same as those performed in step SB1 and step SB2 shown in FIG. 4, although data targeted for processing and details of the processing may be different.

Subsequently, on the conditions that buttons B3, B4, and B5 are specified, the control circuitry 22 performs the processing from step SA2 through step SA6 shown in FIG. 2 for each of an attenuation rate, a normalized local variance, and a hepato-renal echo contrast in this order. The operations of the control circuitry 22 and related circuitry when an attenuation rate is obtained are the same as those performed in step SB1 and step SB2 shown in FIG. 4, although data targeted for processing and details of the processing may be different. The operations of the control circuitry 22 and related circuitry when a normalized local variance is obtained are the same as those performed in step SB1 and step SB2 shown in FIG. 4, although data targeted for processing and details of the processing may be different.

Figure 6:
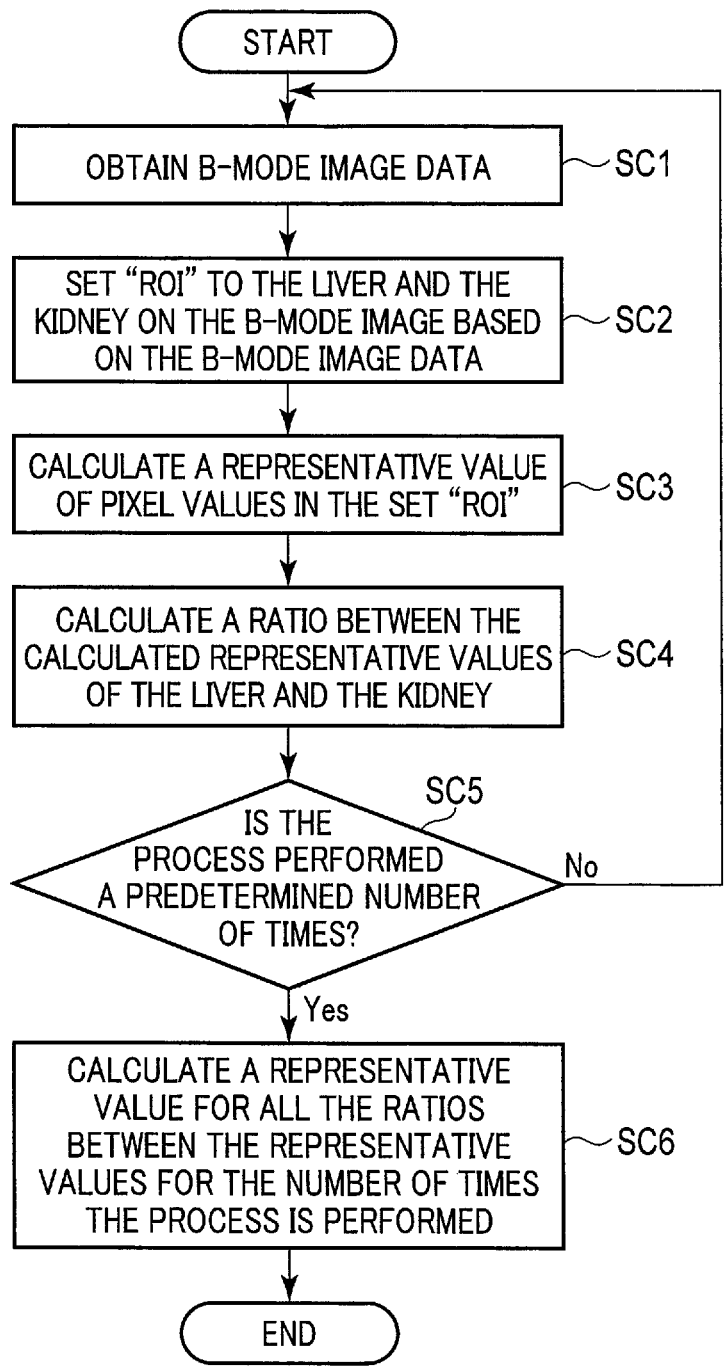
FIG. 6 is a flowchart showing an example of operations of the control circuitry performed when the ultrasound diagnostic apparatus according to the first embodiment obtains quantitative values of tissue properties.

Since the operations of the control circuitry 22 and related circuitry when a hepato-renal echo contrast is obtained may greatly differ from the operations of the control circuitry 22, etc. shown in FIG. 4, the operations are described below. FIG. 6 is a flowchart showing an example of the operations of the control circuitry 22 performed when the ultrasound diagnostic apparatus according to the first embodiment obtains a tissue property parameter. In this case, the tissue property parameter is a hepato-renal echo contrast.

As shown in FIG. 6, the control circuitry 22 controls the ultrasound transmission circuitry 11, ultrasound reception circuitry 12, the B-mode processing circuitry 13, and the image generation circuitry 15, based on the workflow information used for obtaining a hepato-renal echo contrast to generate B-mode image data (step SC1).

The control circuitry 22 sets a region of interest in the liver and the kidney shown in the B-mode image which is generated based on the obtained B-mode image data (step SC2).

The control circuitry 22 calculates a representative value of pixel values in each of the regions of interest set for each of the liver and the kidney (step SC3).

The control circuitry 22 calculates a ratio between the representative values calculated for the liver and the kidney (step SC4).

The control circuitry 22 determines whether or not the processing from step SC1 through step SC4 is performed a predetermined number of times, for example, five times (step SC5).

If it is determined that the processing from step SC1 through step SC4 is not performed the predetermined number of times (No in step SC5), the control circuitry 22 repeats the processing from step SC1 through step SC4 until the processing is performed the predetermined number of times.

If it is determined that the processing from step SC1 through step SC4 is performed the predetermined number of times (Yes in step SC5), the control circuitry 22 calculates a representative value of the calculated ratios of the representative values of the liver and the kidney for said predetermined number of times, for example five times (step SC6). By this process, a hepato-renal echo contrast is obtained.

The regions of interest in the liver and the kidney may be manually set via the input interface circuitry 20 in step SC2.

According to FIG. 2, if it is determined that no other tissue property parameters need to be acquired, in other words, if all of a modulus of elasticity, a viscosity coefficient, an attenuation rate, a normalized local variance, and a hepato-renal echo contrast are obtained (No in step SA6), the control circuitry 22 retrieves multiple thresholds for each of the parameters from the internal memory circuitry 17. The control circuitry 22 then generates radar chart data expressing tissue characterization support information by using the obtained tissue property parameters and the thresholds respectively retrieved for tissue properties (step SA7).

When button B6 (shown in FIG. 3) is specified for example, the control circuitry 22 executes the display control function 227 and causes the display device 50 to display a radar chart based on the generated radar chart data (step SA8).

FIG. 7 is a diagram showing an example of a radar chart displayed on the display device 50 according to the first embodiment. The radar chart shown in FIG. 7 shows the stages which each of the obtained modulus of elasticity, viscosity coefficient, attenuation rate, normalized local variance, and hepato-renal echo contrast has reached.

Specifically, according to FIG. 7, the obtained modulus of elasticity, viscosity coefficient, attenuation rate, normalized local variance, and hepato-renal echo contrast are plotted respectively on lines L1, L2, L3, L4, and L5, in accordance with the obtained values. Each of the plotted points is connected to its adjacent points by lines. A pentagon P1 is thereby formed.

According to the radar chart shown in FIG. 7, four thresholds are set for each of the obtained modulus of elasticity, viscosity coefficient, attenuation rate, normalized local variance, and hepato-renal echo contrast Specifically, for the modulus of elasticity, four thresholds, $E_0$, $E_1$, $E_2$, and $E_3$, are displayed on line L1. The thresholds on line L1 satisfy the relationship $E_0<E_1<E_2<E_3$, for example. For the viscosity coefficient, four thresholds, $D_0$, $D_1$, $D_2$, and $D_3$, are displayed on line L2. The thresholds on line L2 satisfy the relationship $D_0<D_1<D_2<D_3$, for example. Specifically, for the attenuation rate, four thresholds, $A_0$, $A_1$, $A_2$, and $A_3$, are displayed on line L3. The thresholds on line L3 satisfy the relationship $A_0<A_1<A_2<A_3$, for example. For the normalized local variance, four thresholds, $N_0$, $N_1$, $N_2$, and $N_3$, and are displayed on the line L5. The relationship of the thresholds on line L5 is, for example, $N_0<N_1<N_2<N_3$, if the ROI is observed in instances where liver fibrosis is suspected. For the hepato-renal echo contrast, four thresholds, $R_0$, $R_1$, $R_2$, and $R_3$, are displayed on line L4. The thresholds on line L4 satisfy the relationship $R_0<R_1<R_2<R_3$, for example.

According to FIG. 7, it is possible to know a stage of each tissue property parameter in accordance with the relationship between each of the plotted quantitative values and the thresholds that is set for each tissue property parameter. In FIG. 7, a level-1 stage indicating that a degree of progression is low, a level-2 stage indicating that a degree of progression is intermediate, a level-3 stage indicating that a degree of progression is high, and a level-4 stage indicating that a degree of progression is higher than level 3 are respectively displayed in blue, green, brown, and white, as shown in legends. The above-described stages indicate that cut-off values of fibrosis stages F11 through F14 are allocated to level 1 ($E_0$) to level 4 ($E_3$), for example. The number of stages is not always four, and the number of stages may be changed for each type of tissue properties. The examples shown in FIG. 7 and thereafter will be described on the assumption that each of the parameters is divided into four stages.

According to FIG. 7, the regions where the modulus of elasticity, the viscosity coefficient, the attenuation rate, the normalized local variance, and the hepato-renal echo contrast are respectively $E_0$, $D_0$, $A_0$, $N_0$, and $R_0$ or lower, are displayed in blue as a level-1 stage. As for the normalized local variance, if the ROI is observed with respect to a fatty liver, a threshold is set in such a manner that the value approximates to 1 as the thresholds become away from the center O on line L4, for example.

According to FIG. 7, the region where $E_0<$(the modulus of elasticity)$\leq E_1$, $D_0<$(the viscosity coefficient)$\leq D_1$, $A_0<$(the attenuation rate)$\leq A_1$, $N_0<$(the normalized local variance) $\leq N_1$, and $R_0<$(the hepato-renal echo contrast)$\leq R_1$ is displayed in green as a level-2 stage.

Further according to FIG. 7, the region where $E_1<$(the modulus of elasticity)$\leq E_2$, $D_1<$(the viscosity coefficient) $\leq D_2$, $A_1<$(the attenuation rate)$\leq A_2$, $N_1<$(the normalized local variance)$\leq N_2$, and $R_1<$(the hepato-renal echo contrast) $\leq R_2$ is displayed in brown as a level-3 stage.

In FIG. 7, the region outside of the region indicated as the level-3 stage is displayed in white as a level-4 stage.

Figure 8:
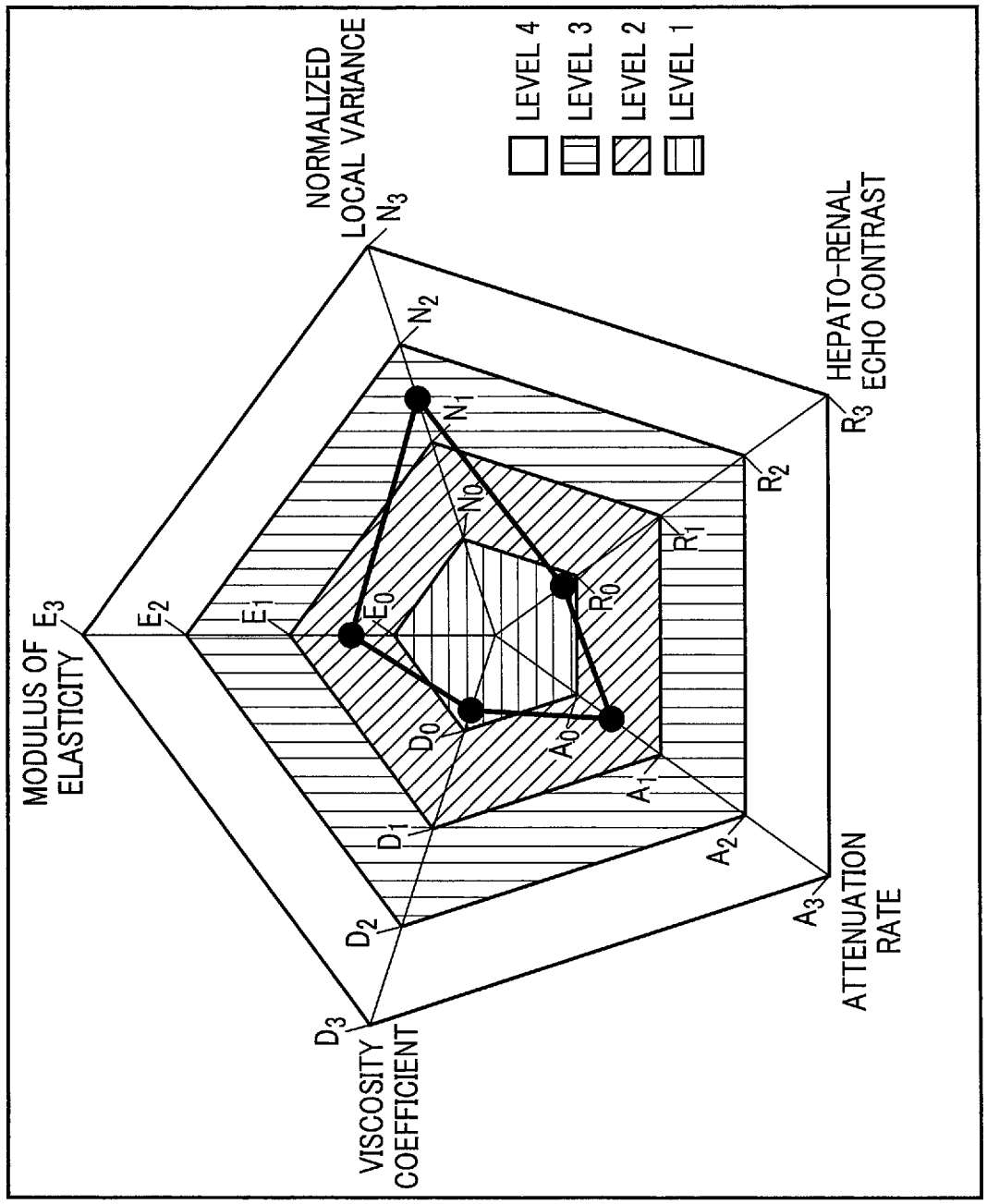
FIG. 8 is a diagram showing another example of the radar chart displayed on the display device according to the first embodiment.

The control circuitry 22 may emphasize points plotted in accordance with the obtained quantitative values of tissue properties by displaying the points as black dots. FIG. 8 is a diagram showing another example of a radar chart displayed on the display device 50 according to the first embodiment. According to FIG. 8, the quantitative values of tissue properties are displayed as black dots for emphasis at respective locations in accordance with the quantitative values. The displayed points are connected to their adjacent points by lines. The lines connecting the points may be dashed lines. Different types of dashed lines may be used for different purposes. Solid lines and dashed lines may be mixed in use in the display of the radar chart.

If the obtained tissue property parameter becomes larger than a value corresponding to the level-4 stage, the control circuitry 22 may display the radar chart in a manner as will be described below.

Figure 9:
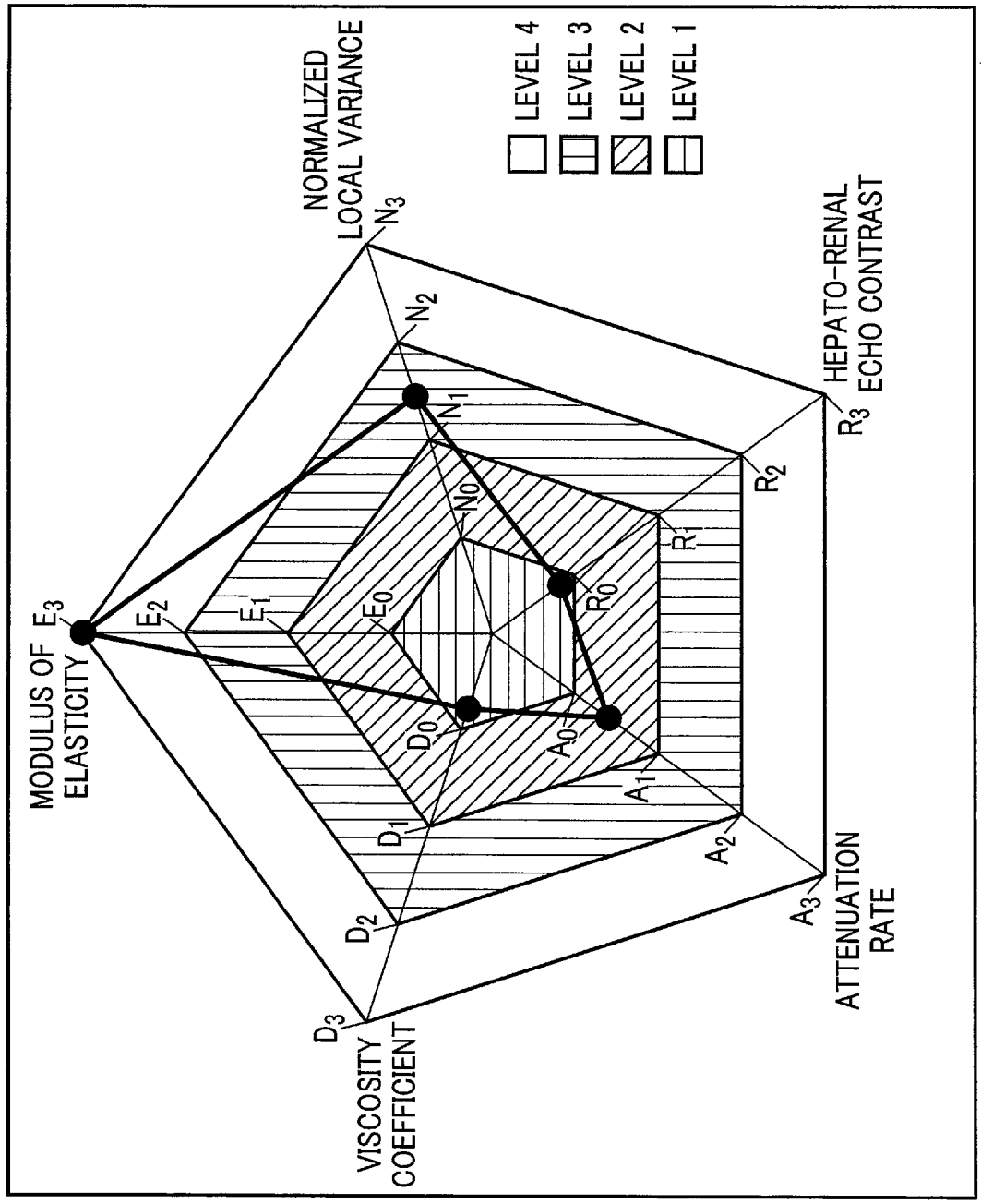
FIG. 9 is a diagram showing another example of the radar chart displayed on the display device according to the first embodiment.

For example, the control circuitry 22 generates radar chart data defining the tissue property parameter that is larger than a value corresponding to the level-4 stage as a maximum value to be displayed on the radar chart. The control circuitry 22 causes the display device 50 to display a radar chart based on the generated radar chart data. FIG. 9 is a diagram showing an example of a radar chart displayed on the display device 50 according to the first embodiment. According to the radar chart shown in FIG. 9, the obtained modulus of elasticity is equal to or larger than a value corresponding to the level-4 stage, and the modulus of elasticity is therefore displayed at $E_3$.

As another example, the control circuitry 22 generates radar chart data defining the tissue property parameter that is larger than a value corresponding to the level-4 stage to be plotted outside of the radar chart. The control circuitry 22 causes the display device 50 to display a radar chart based on the generated radar chart data.

Figure 10:
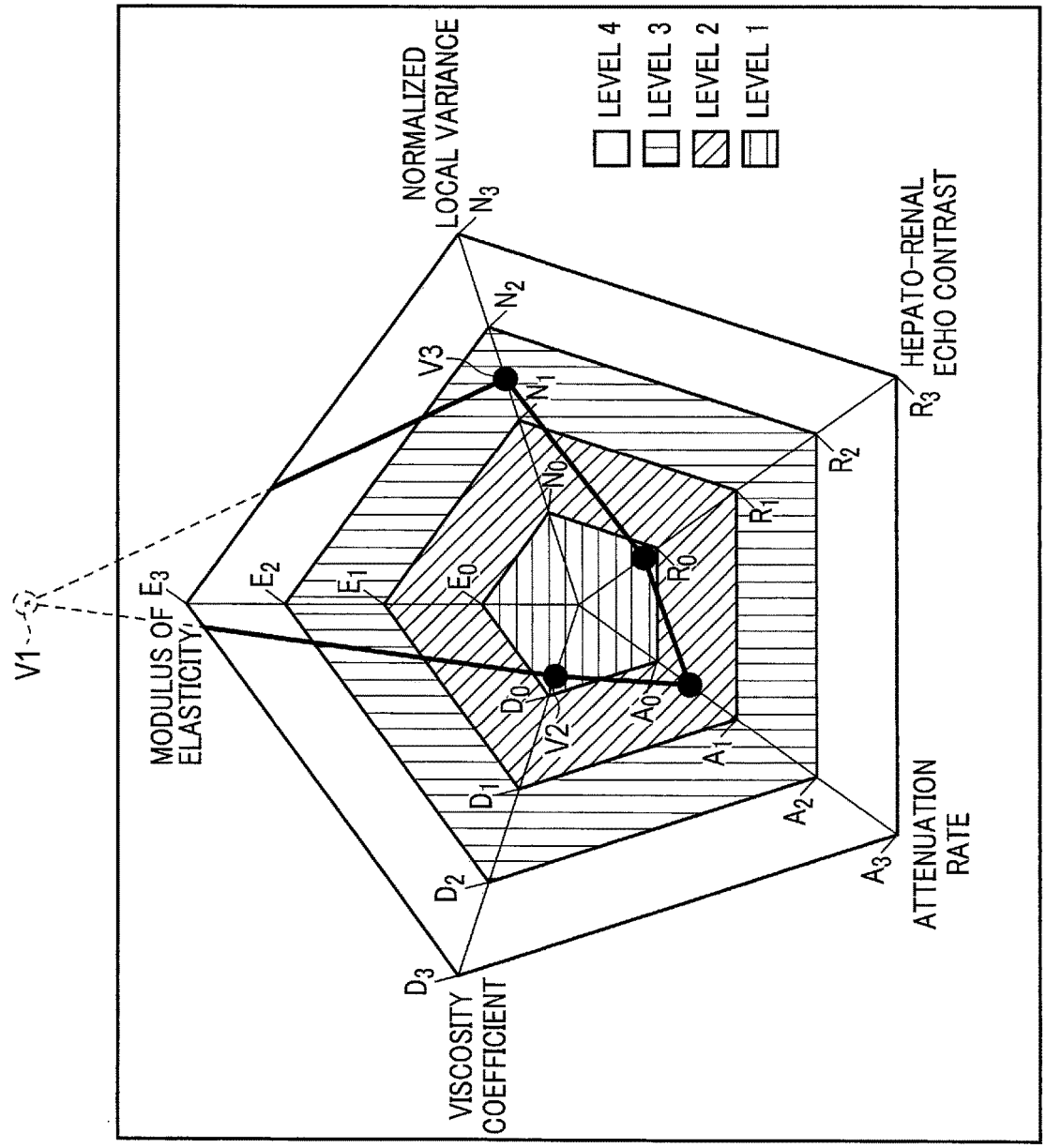
FIG. 10 is a diagram showing a further example of the radar chart displayed on the display device according to the first embodiment.

FIG. 10 is a diagram showing an example of a radar chart displayed on the display device according to the first embodiment. According to FIG. 10, the control circuitry 22 generates radar chart data defining the obtained modulus of elasticity to be plotted outside of the radar chart, namely at point V1 which is located outside the point indicating the threshold $E_3$. In this case, in FIG. 10, the control circuitry 22 displays the solid-line portion of line V1-V2, connecting point V1 and point V2 and indicating the obtained modulus of chart shown inside the radar chart, and does not display the dashed-line portion of line V1-V2 outside of the radar chart. In FIG. 10, the control circuitry 22 displays the solid-line portion of line V1-V3, connecting point V1 and point. V3 and indicating the obtained normalized local variance shown inside the radar chart, and does not display the dashed-line portion of line V1-V3 outside of the radar chart.

According to the first embodiment, the control circuitry 22 obtains quantitative values of tissue properties relating to an ROI of the subject P. The control circuitry 22 generates diagram data (radar chart data) relating to a designated ROI based on the obtained quantitative values.

It is thereby possible to know the tissue properties of the subject by the shape and size, etc. of graphics expressed by a polygonal shape, such as a pentagon. Since multiple thresholds are set for each tissue property type, it is possible to know the stage which the quantitative value of each tissue property type has reached. In other words, a diagnostician can conduct diagnosis from various points of view, compared to a case where only a single tissue property parameter corresponding to one tissue property type is provided.

Accordingly, it is possible to preferably present a plurality of types of quantified tissue properties.

First Modification

The control circuitry 22 of the first embodiment generates radar chart data of a radar chart similar to the one shown in FIG. 7, for example; however, the control circuitry 22 is not limited thereto. For example, the control circuitry 22 may generate diagram data of a diagram presenting a single case. In the following description of the first modification, let us suppose that the internal memory circuitry 17 stores, in advance, case information associated with a plurality of types of tissue properties. The case information includes a reference value to be compared with a particular tissue property parameter. Parameters of a plurality of types of tissue properties are a modulus of elasticity, a viscosity coefficient, an attenuation rate, a local dispersion variance, and a hepato-renal echo contrast, and the quantitative values thereof are 12 [kPa], 0.001 [Pa·s], 1.6, 0.62 [dB/cm/MHz], and 1.2, respectively.

In the first modification, the control circuitry 22 shown in FIG. 1 retrieves the case information associated with the obtained tissue properties from the internal memory circuitry 17 in step SA7 shown in FIG. 2, for example. The control circuitry 22 then generates diagram data presenting a single case based on the quantitative values of the tissue properties and the case information associated with each of the tissue properties.

Specifically, the control circuitry 22 compares, for example, the modulus of elasticity with the reference value included in the case information associated with the tissue property of elasticity, and extracts a candidate for relevant disease from the case information associated with elasticity. The same processing is performed for the tissue properties other than the elasticity. The control circuitry 22 determines a case to be presented based on the extracted candidate of disease. Diagram data that includes information about a determined case and a process of determining the case is thereby generated.

Figure 11:
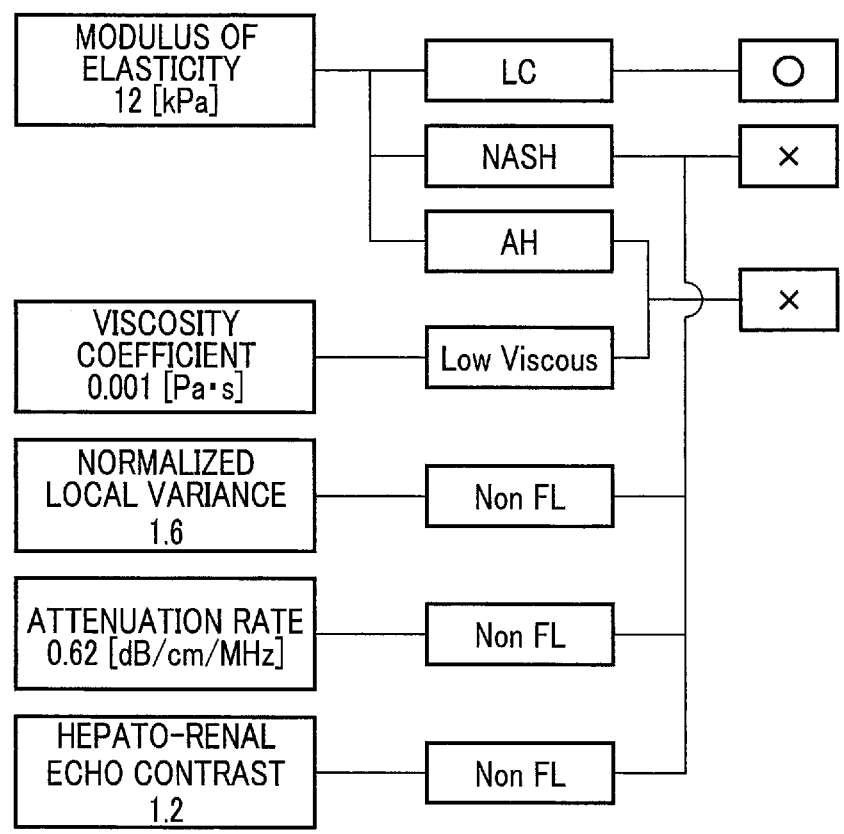
FIG. 11 is a diagram showing an example of a diagram presenting a case displayed on a display device according to a first modification of the first embodiment.

Subsequently, in step SA8 shown in FIG. 2, the control circuitry 22 shown in FIG. 1 causes the display device 50 to display the diagram presenting the case based on the generated diagram data. FIG. 11 is a diagram showing an example of a diagram presenting a case displayed on the display device 50 according to the first modification. In the left column of the diagram shown in FIG. 11, the modulus of elasticity, the viscosity coefficient, the normalized local variance, the attenuation rate, and the hepato-renal echo contrast are displayed. Specifically, the modulus of elasticity is 12 [kPa], the viscosity coefficient is 0.001 [Pa·s], the normalized local variance is 1.6, the attenuation rate is 0.62 [dB/cm/MHz], the hepato-renal echo contrast is 1.2.

In the center column of the diagram shown in FIG. 11, predetermined case information respectively associated with the tissue properties is displayed. Specifically, for the modulus of elasticity, "LC" representing liver cirrhosis, "NASH" representing non-alcoholic steato hepatitis, and "AH" representing acute hepatitis are associated and displayed as candidates of disease.

For the viscosity coefficient, the normalized local variance, the attenuation rate, and the hepato-renal echo contrast, supplementary information for specifying a disease is respectively associated. Specifically, "Low Viscous" representing low viscosity is associated with the viscosity coefficient. As for the normalized local variance, the attenuation rate, and the hepato-renal echo contrast, "Non FL" representing the subject not having a fatty liver (FL) is associated.

In the right column of the diagram shown in FIG. 11, the applicable disease candidates among the list are displayed in the center column of the diagram shown in FIG. 11. Specifically, "NASH" among the disease candidates is not applicable because the normalized local variance, the attenuation rate, and the hepato-renal echo contrast are associated with "Non FL". For this reason, "X" is displayed in the right column of the diagram shown in FIG. 11. "AH" is not applicable because the viscosity coefficient is associated with "Low Viscous". For this reason, "X" is displayed in the right column of the diagram shown in FIG. 11. "LC" is determined to be applicable because the other disease candidates, "NASH" and "AH", are not applicable. For this reason, "O" is displayed in the right column of the diagram shown in FIG. 11. In other words, this illustrated case is one of the cases diagnosed with "LC", and the diagram shown in FIG. 11 shows that liver cirrhosis is suspected for the ROI of the subject P.

If a disease candidate is applicable, "O" is displayed, and if a disease candidate is not applicable, "X" is displayed; however, a different method of display may be adopted as long as it can show whether or not a disease candidate is applicable. For example, "Y" standing for "YES" and "N" standing for "NO" may be displayed to show whether or not a disease candidate is applicable. As another example, check box may be applicable disease candidate and a box labeled with a not-applicable disease candidate may be displayed in different colors.

The diagram shown in FIG. 11 may be displayed along with the radar chart shown in FIG. 7, for example.

According to the first modification, the control circuitry 22 generates diagram data presenting a single case based on tissue properties and case information which is associated with each of the tissue properties. It is thereby possible for a diagnostician to conduct a diagnosis by referring to a case presented.

Second Modification

In the first embodiment, the control circuitry 22 generates diagram data using five tissue property parameters, which are a modulus of elasticity, a viscosity coefficient, an attenuation rate, a normalized local variance, and a hepato-renal contrast. However, what is used to generate diagram data is not limited to the tissue property parameters. The control circuitry 22 may generate diagram data including categories, such as the thickness of the abdominal wall of the subject and the blood test result of the subject, in addition to the categories (items) regarding the tissue properties. In the following description of the second modification, the control circuitry 22 calculates radar chart data based on the four tissue property parameters, which are a modulus of elasticity, a viscosity coefficient, an attenuation rate, and a normalized local variance, and the thickness of the abdominal wall. That is, a modulus of elasticity, a viscosity coefficient, an attenuation rate, a normalized local variance, and an abdominal wall thickness are the five items of the radar chart.

In the first embodiment, the control circuitry 22 retrieves a plurality of threshold values of each tissue property parameter stored in the internal memory circuitry 17, and displays a radar chart showing the stage which each of the obtained tissue property parameters has reached. However, the first embodiment is not limited to the displaying of a stage based on a threshold value. The control circuitry 22 retrieves, from the internal memory circuitry 17, statistical values, such as tissue property parameters for each case (e.g., normal liver, fatty liver, and liver cirrhosis) obtained in the past by the ultrasound diagnostic apparatus 1 or other ultrasound diagnostic apparatus, and generates trend map data (diagram data representing trend) based on the statistical values of each case. In the following description of the second modification, the control circuitry 22 retrieves, from the internal memory circuitry 17, statistical values for each case, i.e., four tissue property parameters, which are a modulus of elasticity, a viscosity coefficient, an attenuation rate, and a normalized local variance, and a thickness of the abdominal wall for each case, and generates trend map data representing the retrieved statistical values for each case.

Figure 12:
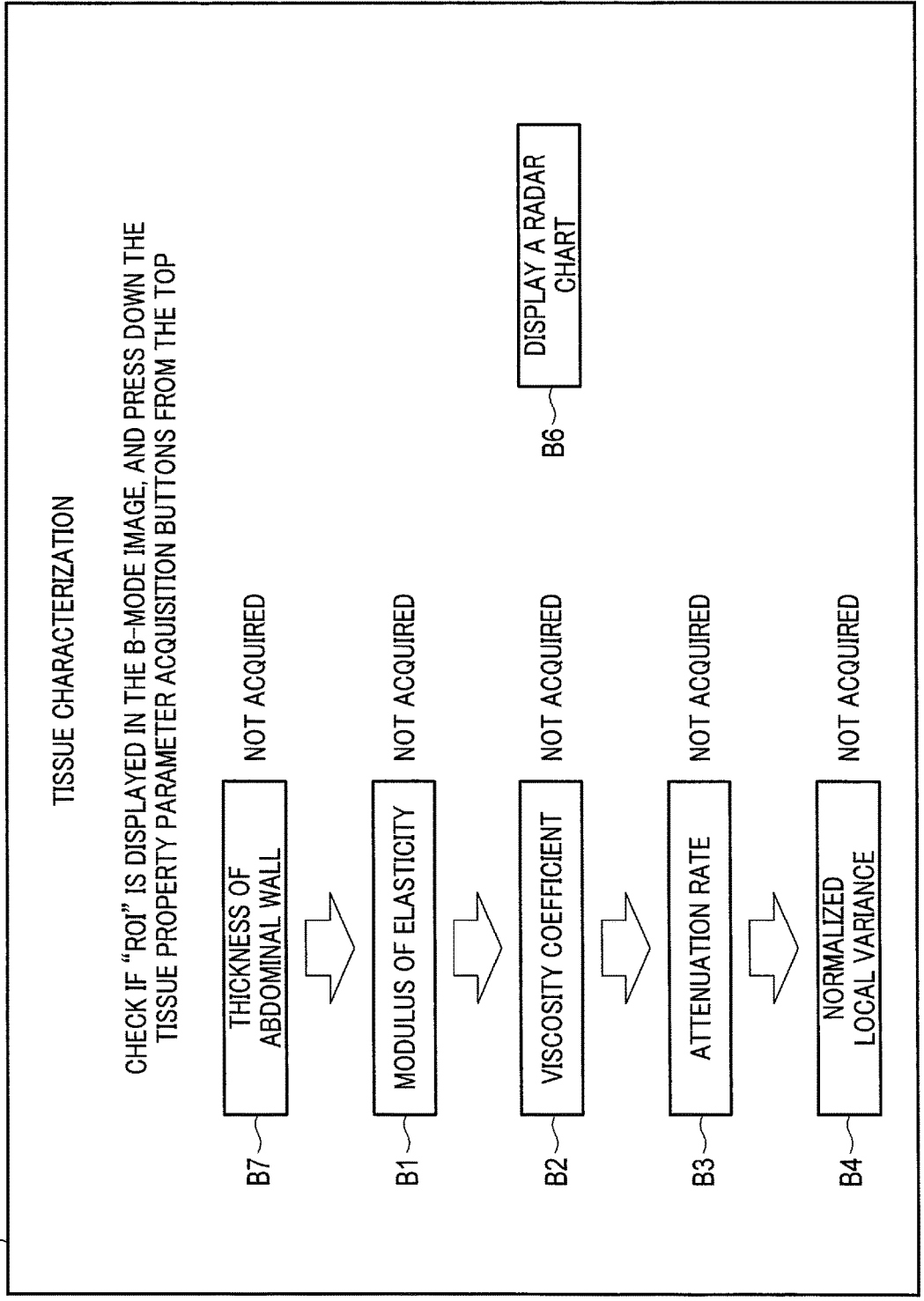
FIG. 12 is a diagram showing an example of workflow information displayed on a display device according to a second modification of the first embodiment.

FIG. 12 is a diagram showing an example of workflow information displayed on the display device 50 according to the second modification. FIG. 12 shows the tissue characterization support screen that guides an operator to obtain the four above-mentioned tissue property parameters and the thickness of the abdominal wall, and displays a radar chart used for a diagnosis of tissue properties. On the tissue characterization support screen shown in FIG. 12, button B7, capable of acquiring the thickness of the abdominal wall used for generation of radar chart data for a tissue characterization, is displayed along with buttons B1, B2, B3, and B4. This makes it possible for the operator to acquire a thickness of the abdominal wall, and the quantitative values of tissue properties, namely a modulus of elasticity, a viscosity coefficient, an attenuation rate, and a normalized local variance, in this order.

Figure 13:
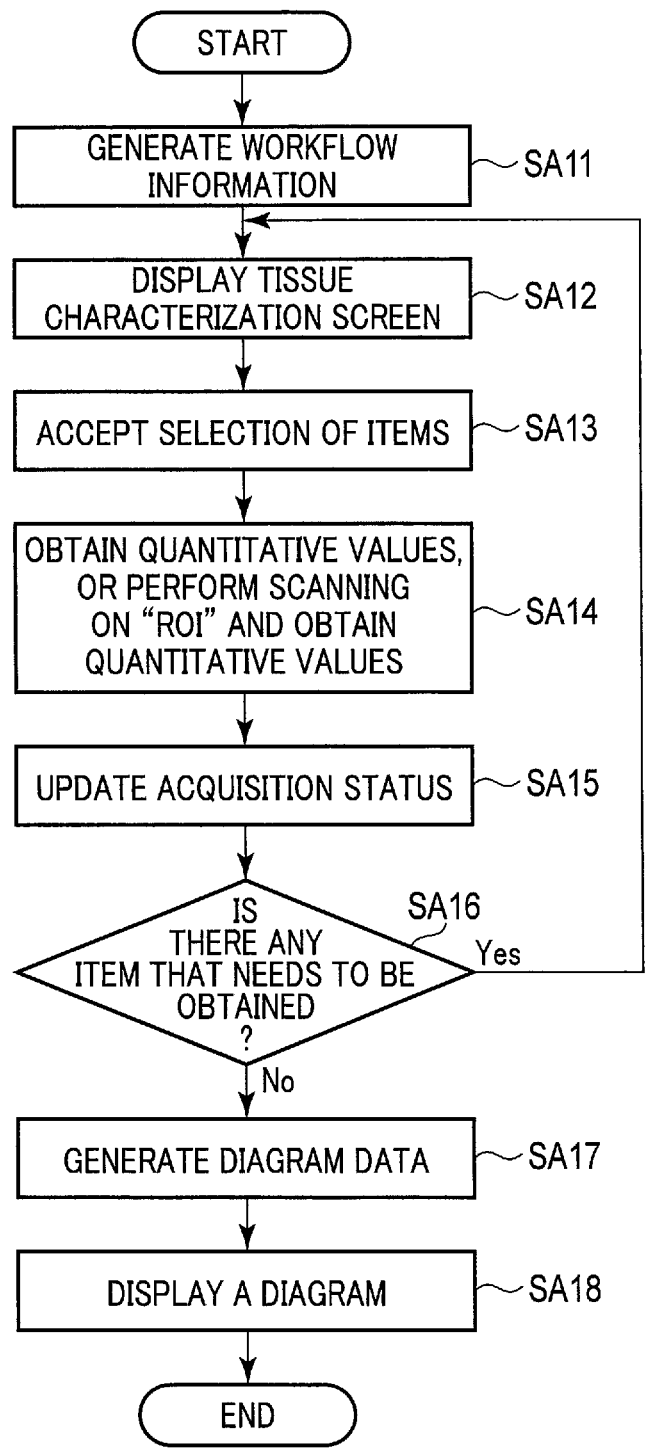
FIG. 13 is a flowchart showing operations of control circuitry performed when the ultrasound diagnostic apparatus according to the second modification generates a diagram related to a tissue characterization.

FIG. 13 is a flowchart showing an example of the operations of the control circuitry 22 performed when the ultrasound diagnostic apparatus 1 according to the second modification generates a diagram related to a tissue characterization. Hereinafter, differences from the first embodiment will mainly be described, and a detailed description of similar points will be omitted. In the second modification, the items listed in a radar chart are a thickness of the abdominal wall, a modulus of elasticity, a viscosity coefficient, an attenuation rate, and a normalized local variance.

Similarly to step SA1, for each item, the control circuitry 22 generates workflow information representing an acquisition procedure for acquiring the items (step SA11). Next, similarly to step SA2, the control circuitry 22 displays a tissue characterization support screen, like the one shown in FIG. 12 (step SA12). Then, the control circuitry 22 accepts selection of items for which quantitative values are acquired (step SA13). At this time, in FIG. 12, let us suppose that the tissue property parameters are selected in the order of buttons B7, B1, B2, B3, and B4.

If button B7 is specified in step SA13, the control circuitry 22 obtains a thickness of the abdominal wall based on workflow information used for obtaining a thickness of the abdominal wall (step SA14). For example, the control circuitry 22 can measure the thickness of the abdominal wall in advance on the B-mode image by the caliper function of the control circuitry 22, after the B-mode image is frozen in the B-mode image display. The measured thickness value of the abdominal wall may be stored in the internal memory circuitry 17. The control circuitry 22 acquires the thickness of the abdominal wall by retrieving the thickness value of the abdominal wall from the internal memory circuitry 17 in step SA14. Alternatively, the control circuitry 22 may acquire the thickness of the abdominal wall manually entered by the operator with the input device 60 via the input interface circuitry 20. For example, when button B7 is specified, a screen for entering the thickness of the abdominal wall is displayed, and the operator may input the thickness of the abdominal wall using the input device 60. The thickness value of the abdominal wall that is manually input is equal to the previously-measured thickness of the abdominal wall acquired by the caliper function after the B-mode image is frozen in the B-mode image display.

When acquiring the thickness of the abdominal wall in step SA14 shown in FIG. 13, the control circuitry 22 updates the acquisition status regarding the thickness of the abdominal wall from "not acquired" to "acquired," in the same manner as in step SA5 (Step SA15). The control circuitry 22 determines whether or not there are other items that need to be acquired (step SA16). The control circuitry 22 repeats the processing from step SA12 to step SA16 until it is determined that there is no other item to be acquired.

If it is determined that no other items need to be acquired, in other words, if all of a thickness of the abdominal wall, a modulus of elasticity, a viscosity coefficient, an attenuation rate, a normalized local variance, and a hepato-renal echo contrast have been acquired (No in step SA16), the control circuitry 22 retrieves statistical values of those parameters for each case from the internal memory circuitry 17. The control circuitry 22 then generates diagram data representing tissue characterization support information by using the acquired items and the statistical values for each case corresponding to the items (step SA17), and causes the display device 50 to display a diagram based on the generated diagram data (step SA18).

Figure 16:
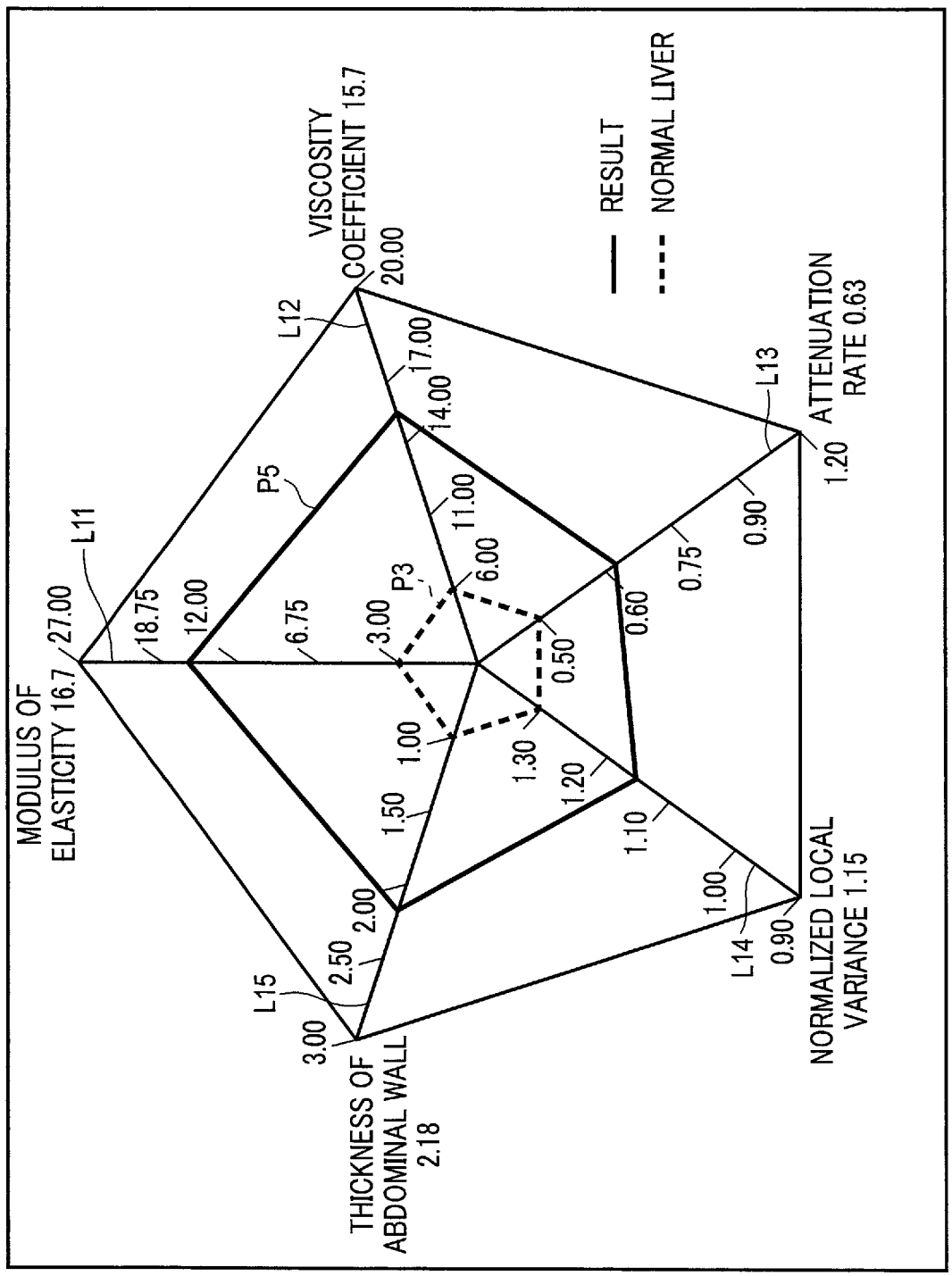
FIG. 16 is a diagram showing an example of a radar chart displayed on the display device according to the second modification.

FIGS. 14 to 16 are diagrams showing an example of a radar chart displayed on the display device 50 according to the second modification. In the radar charts shown in FIGS. 14 to 16, the thicknesses of the abdominal wall, the modulus of elasticity, the viscosity coefficient, the attenuation rate, and the normalized local variance, which are the acquired quantitative values, are respectively plotted on the line L11, L12, L13, L14, and L15, and pentagons P2, P4 and P5, acquired by connecting these values by solid lines, are shown in the respective figures. In the chart, each item is displayed along with a numerical value indicating the quantitative value of the item, and each line is marked with a graduation. Also, in each of the figures, pentagon P3 is shown as a trend map display based on the statistical values (empirical values), in which the values corresponding to the statistical values of the items in normal liver are connected by a dashed line. The lines of pentagons P2, P3, P4, and P5 may be a solid line or a dashed line, or may be distinguished by different colors.

For example, a pentagon similar to pentagon P3 based on the statistical values of normal liver, such as pentagon P2 in the radar chart shown in FIG. 14, represents the case of a normal liver.

In each of the radar charts shown in FIGS. 14 to 16, among the five items of the radar chart, the modulus of elasticity and the viscosity coefficient are arranged adjacent to each other, for example, at the top side of the radar chart. For example, a modulus of elasticity is placed at the topmost position and viscosity coefficient is placed adjacent to it. That is, the control circuitry 22 generates diagram data so that the modulus of elasticity and the viscosity coefficient are displayed at adjacent positions on the diagram by the diagram data generation function.

The attenuation rate and the normalized local variance are arranged adjacent to each other, for example, at the bottom side of the radar chart. For example, the attenuation rate and the normalized local variance are arranged in the bottom. That is, the control circuitry 22 generates diagram data so that the attenuation rate and the normalized local variance are displayed at adjacent positions on the diagram by the diagram data generation function. The thickness of the abdominal wall is located next to the normalized local variance in this example. The thickness of the abdominal wall may be placed next to the attenuation rate. For example, in the radar charts shown in FIGS. 14 to 16, the viscosity coefficient and the thickness of the abdominal wall may be interchanged.

It is known that fatty liver correlates with an attenuation rate and a normalized local variance among the above-mentioned tissue property parameters. If the acquired quantitative values for the attenuation rate and the normalized local variance are large, there is a tendency to diagnose a subject as having fatty liver. Since the thickness of the abdominal wall represents the thickness of the subcutaneous fat, a large thickness value of the abdominal wall leads to a tendency to diagnose a subject as having fatty liver. Therefore, the control circuitry 22 generates radar chart data in which the attenuation rate, the normalized local variance, and the thickness of the abdominal wall, for example, are arranged together in the bottom side, and causes the display device 50 to display a radar chart based on the generated radar chart data. The control circuitry 22 generates diagram data by, for example, the diagram generation function, so that any two or more of the attenuation rate, the normalized local variance, and the thickness value of the abdominal wall are displayed at adjacent positions on the diagram. For example, a pentagon spreading downward such as pentagon P4 of the radar chart shown in FIG. 15 represents the case of a fatty liver.

On the other hand, it is known that liver cirrhosis correlates with a modulus of elasticity and a viscosity coefficient among the above-mentioned tissue property parameters. If the acquired quantitative values for the modulus of elasticity and the viscosity coefficient are large, there is a tendency to diagnose a subject as having liver cirrhosis. Therefore, the control circuitry 22 generates radar chart data in which the modulus of elasticity and the viscosity coefficient, for example, are arranged together in the top side, and causes the display device 50 to display a radar chart based on the generated radar chart data. For example, a pentagon spreading upward such as pentagon P5 of the radar chart shown in FIG. 16 represents the case of a liver cirrhosis.

As described above, the control circuitry 22 generates, by the diagram generation function, a diagram by using the arrangement of the quantitative values of the respective tissue properties shown on the diagram, based on the information on the relationship among the quantitative values of the plurality of types of tissue properties. The generation of radar chart data in which the correlated attribute items are arranged side by side for each case makes it possible to display radar chart which allows more intuitive diagnosis.

Figure 17:
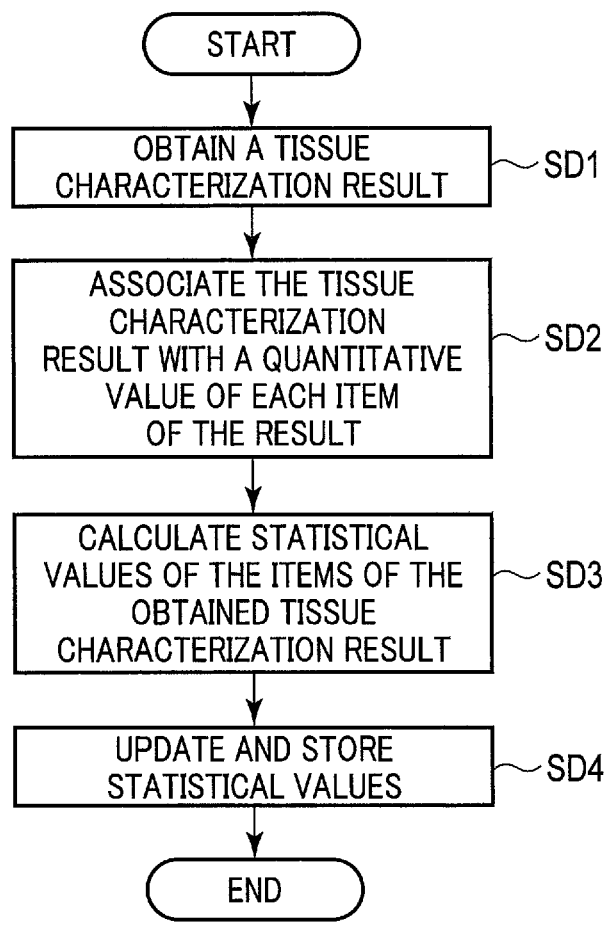
FIG. 17 is a flowchart showing operations of the control circuitry performed when statistical values based on a diagnosis result obtained by the ultrasound diagnostic apparatus according to the second modification are calculated for each case.

FIG. 17 is a flowchart showing an example of the operations of the control circuitry 22 performed when statistical values for each case based on a result of tissue characterization acquired with the use of the ultrasound diagnostic apparatus 1 of the second modification are calculated for each case. The control circuitry 22 accepts input of the tissue characterization result (for example, diseases such as normal liver, fatty liver, liver cirrhosis or the like) via the input interface circuitry 20, and acquires information about the tissue characterization result (step SD1). The control circuitry 22 associates the information about the acquired tissue characterization result with the quantitative value of each item of the radar chart corresponding to the tissue characterization result retrieved from the internal memory circuitry 17 (step SD2). The control circuitry 22 calculates the statistical value of each item of the acquired tissue characterization result (step SD3). For example, the control circuitry 22 retrieves the statistical value of each item corresponding to the tissue characterization result from the internal memory circuitry 17, and calculates a new statistical value of each item from the statistical value and the quantitative value associated with the tissue characterization result in step SD2. The control circuitry 22 updates the statistical value to the calculated new statistical value and saves the new statistical value (step SD4). The control circuitry 22 has the internal memory circuitry 17 store, for example, the new statistical value of each item corresponding to the tissue characterization result.

By updating the statistical value of each case based on the tissue characterization and the quantitative value of each item of the radar chart corresponding to the tissue characterization result, it is possible to generate trend map data useful for conducting the tissue characterization and to display a trend map.

Figure 18:
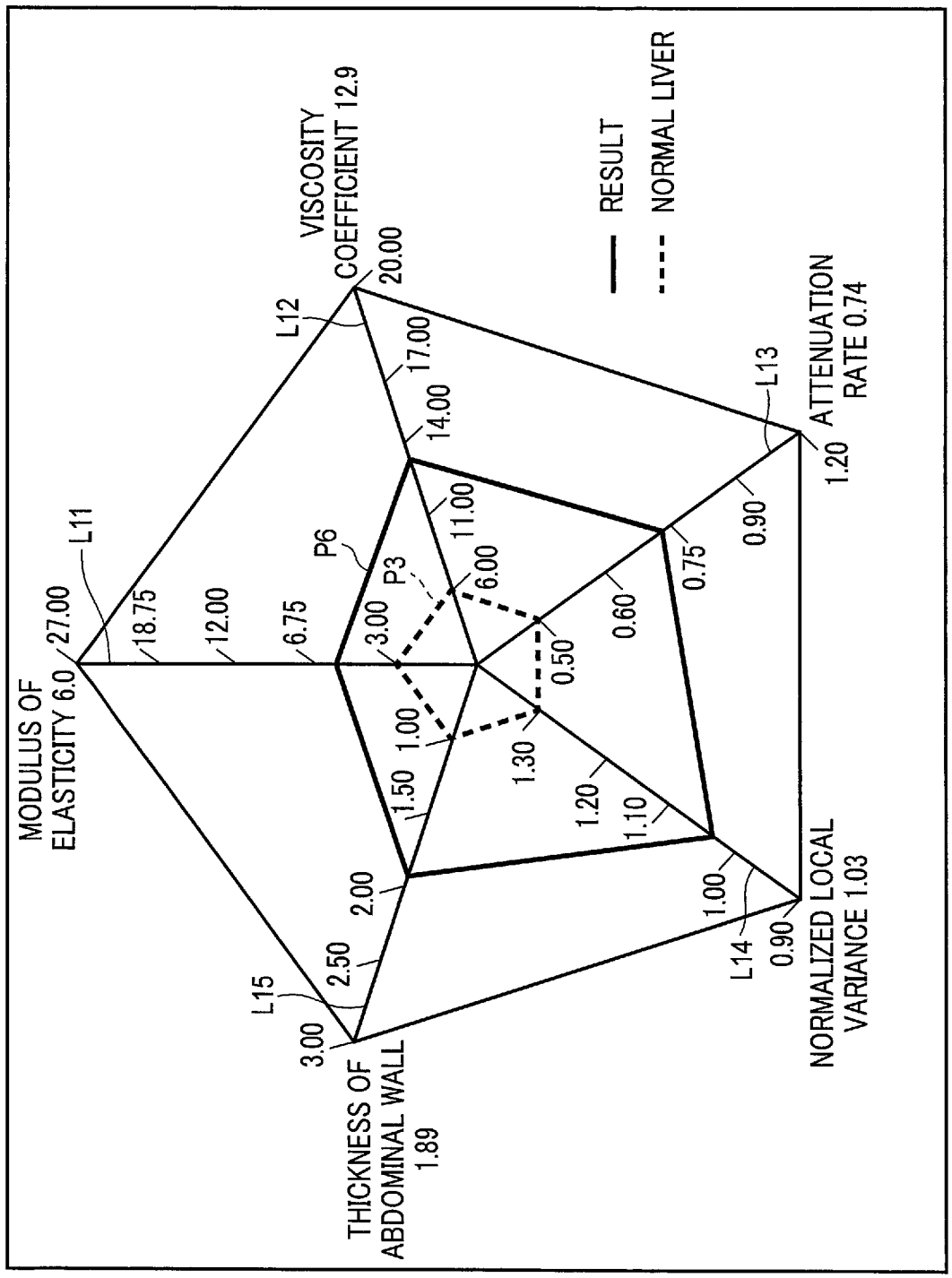
FIG. 18 is a diagram showing an example of a radar chart displayed on the display device according to the second modification.

FIG. 18 is a diagram showing an example of a radar chart displayed on the display device 50 according to the second modification. The radar chart shown in FIG. 18 shows pentagon P6 spreading downward. For this reason, as described above, a fatty liver is suspected in the liver which is a region of interest. In such a case, the operator may switch the display of pentagon P3 representing the trend of a normal liver to the display of pentagon representing the trend of a fatty liver.

FIG. 19 of a flowchart showing an example of the operations of the control circuitry 22 performed when a display of a diagram representing a trend is switched. The control circuitry 22 accepts input of a case (name of suspected disease) via the input interface circuitry 20 and acquires case information specifying a suspected disease (step SE1). Based on the acquired case information, the control circuitry 22 regenerates diagram data representing a trend (step SE2). For example, the control circuitry 22 retrieves the statistical values of the items of the corresponding case from the internal memory circuitry 17 to generate the diagram data representing a trend based on the statistical values. The control circuitry 22 then re-displays a diagram representing the trend based on the generated diagram data (step SE3).

Figure 20:
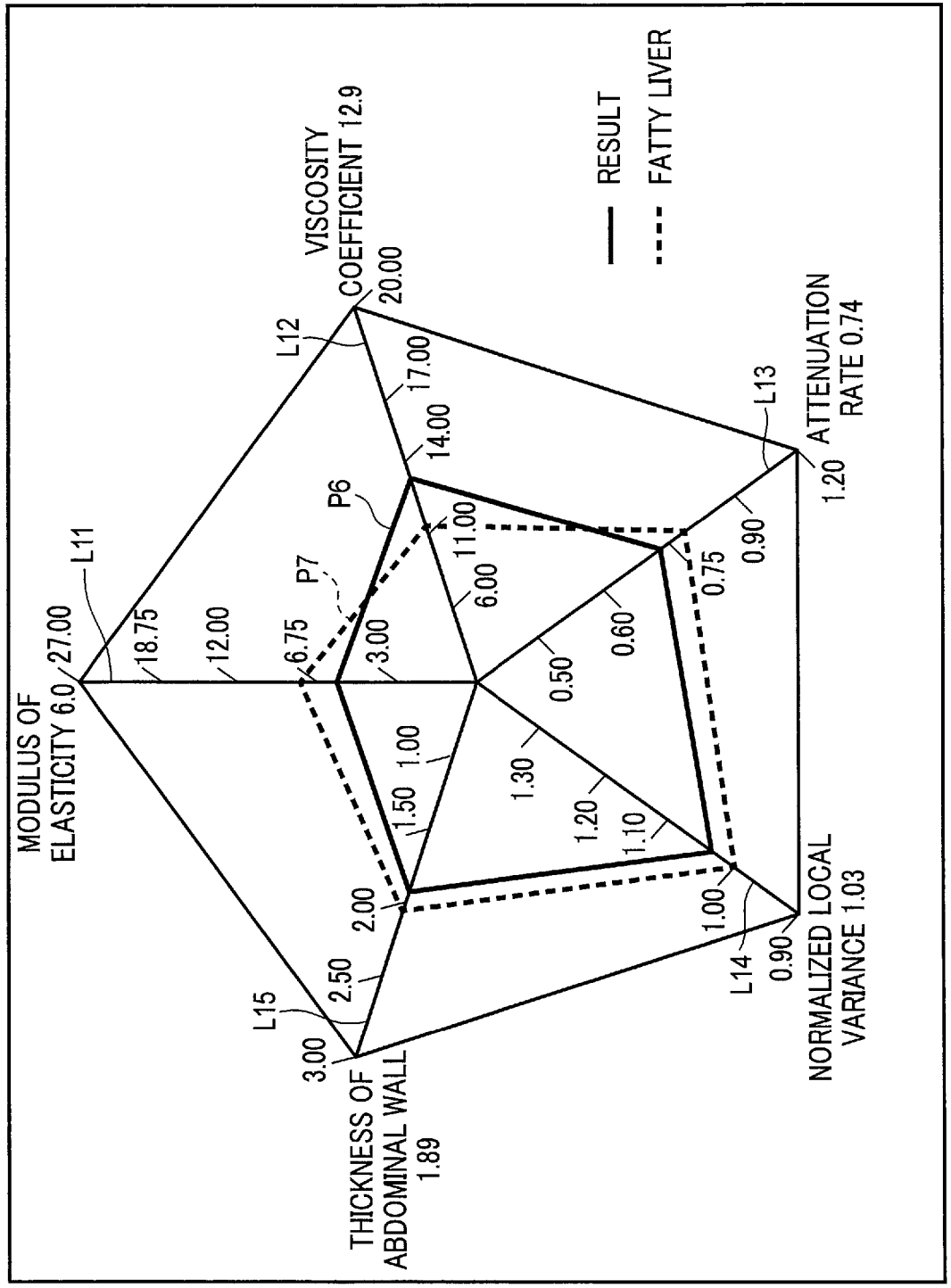
FIG. 20 is a diagram showing an example of a radar chart displayed on the display device according to the second modification.

FIG. 20 is a diagram showing an example of a radar chart displayed on the display device 50 of the second modification. The control circuitry 22 changes the display on the display device 50 by the operations shown in the flowchart of FIG. 19. For example, as the diagram representing the trend in the radar chart, pentagon P3 based on the statistical values of the items in the normal liver shown in FIG. 18 is switched to pentagon P7, shown in FIG. 20, based on the statistical values of the items in the fatty liver. The pentagon P6 in the radar chart shown in FIG. 20 is similar to the pentagon P7 shown based on the statistical values of a fatty liver, which makes it easier to know that a fatty liver is suspected.

In this way, by appropriately changing the display of the trend of each case based on the statistical values, the trend of each case can be displayed. In addition, comparing the diagram showing the trend of each case and the diagram based on the measurement result can contribute to the tissue characterization.

Pentagon P3 shown in FIG. 18 and pentagon P7 shown in FIG. 20 may be simultaneously displayed. The control circuitry 22 may generate a plurality of trend map data each representing a case, and simultaneously display a plurality of trend maps. Alternatively, the control circuitry 22 may generate a plurality of trend map data each representing a case, and automatically display a trend map based on trend map data closest to the measurement result among the generated trend map data. For example, the control circuitry 22 calculates a residual sum of squares for each of the quantitative values of the tissue properties related to the measurement result and the value of the trend map data, and a trend map is displayed based on trend map data in which the calculated residual sum of squares is minimized.

Up to this point, the case where the suspected disease is unknown has been described; however, in the case where the suspected disease is known to some extent, the control circuitry 22 may generate the diagram data suitable for a tissue characterization of the disease and display the diagram. For example, if the operator inputs a suspected disease with the use of the input device 60, radar chart data is generated and a radar chart is displayed with radar chart items suitable for diagnosing the disease.

FIG. 21 is a flowchart showing an example of the operations of the control circuitry 22 performed when a diagram suitable for diagnosis of a suspected disease is generated. The control circuitry 22 accepts input of a case (name of suspected disease) via the input interface circuitry 20 and acquires case information specifying a suspected disease (step SF1). The control circuitry 22 generates diagram data in accordance with the acquired case information (step SF2). When case information indicating "fatty liver" as the suspected disease is acquired, the control circuitry 22 retrieves the quantitative values and statistical values of the attenuation rate, the normalized local variance, and the thickness of the abdominal wall from the internal memory circuitry 17. Then, the control circuitry 22 generates diagram data using the quantitative values and the statistical values. The control circuitry 22 causes the display device 50 to display a diagram based on the generated diagram data (step SF3).

Alternatively, the control circuitry 22 may generate diagram data and display a diagram more suitable for a diagnosis by generating diagram data based on the selected items and displaying a diagram.

FIG. 22 is a flowchart showing an example of the operations of the control circuitry 22 performed when a diagram is generated by selecting items. The control circuitry 22 accepts the selection of items via the input interface circuitry 20 and acquires the information about the selected items (step SG1). The control circuitry 22 generates diagram data in accordance with the acquired item information (step SG2). For example, the control circuitry 22 retrieves the quantitative values and the statistical values corresponding to the information about the acquired items from the internal memory circuitry 17. Then, the control circuitry 22 generates diagram data using the quantitative values and the statistical values. The control circuitry 22 causes the display device 50 to display a diagram based on the generated diagram data (step SG3).

Here, the internal memory circuitry 17 may group items of the radar chart and store them. For example, the control circuitry 22 stores items of the radar chart in the internal memory circuitry 17, dividing the items into a group of modulus of elasticity and viscosity coefficient, which are items useful for diagnosis of liver cirrhosis, a group of attenuation rate, a normalized local variance, and a thickness of the abdominal wall, which are useful for diagnosis of fatty liver. The control circuitry 22 may arrange the items of the radar chart generated in foregoing step SG2 such that the grouped items are adjacent to each other.

The control circuitry 22 may change the items of the radar chart after displaying the radar chart. For example, by increasing the number of acquisition items for which selection is accepted in step SA13 (shown in FIG. 13) to be greater than the number of display items in the radar chart, the control circuitry 22 acquires in advance a larger number of quantitative values than the number of display items in the radar chart. The acquired quantitative values may be stored in the internal memory circuitry 17.

Items other than the quantitative values of the tissue properties in the radar chart may be a result of blood test, for example, a value of FIB-4 index. FIB-4 index is referred to as an index for estimating liver fibrosis. In this case, on the tissue characterization support screen shown in FIG. 12, a button for acquiring a value of FIB-4 index may be displayed instead of button B7 for acquiring the thickness of the abdominal wall. When the button is specified, the control circuitry 22 acquires a value of FIB-4 index based on the workflow information for acquiring a value of FIB-4 index (step SA14, shown in FIG. 13). A result of a blood test such as the value of FIB-4 index may be acquired from the external device 40 capable of communicating with the ultrasound diagnostic apparatus 1 via the network 100, for example a hospital information system (HIS), and stored in the internal memory circuitry 17, or manually input through the input device 60.

Figure 23:
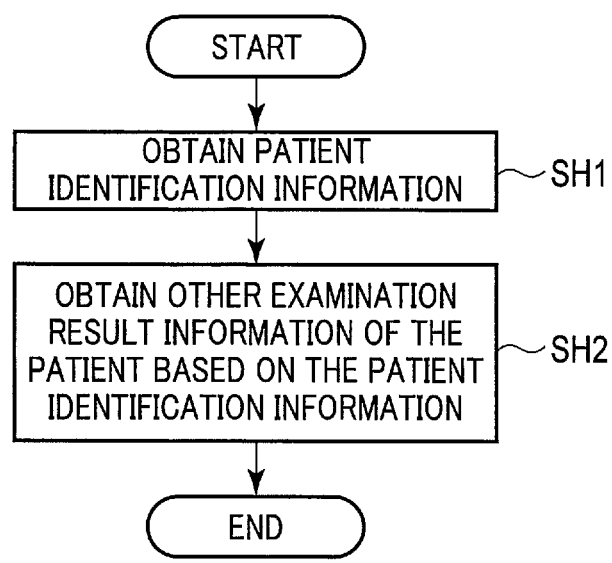
FIG. 23 is a flowchart showing an example of operations of the control circuitry performed when other examination result information is obtained from an external apparatus.

FIG. 23 is a flowchart showing an example of the operations of the control circuitry 22 performed when other examination result information is acquired from the external apparatus 40. The control circuitry 22 retrieves, for example, patient identification information, which is a patient ID from the internal memory circuitry 17, and transmits said patient identification information to the external device 40 (step SH1). The control circuitry 22 acquires other examination result information corresponding to the patient identification information, for example blood test information, from the external device 40, for example, the hospital information system (step SH2).

It is known that the value of FIB-4 index correlates with liver cirrhosis. If the value of FIB-4 index is large, liver cirrhosis is suspected. Therefore, when FIB-4 index is adopted as an item of radar chart, the control circuitry 22 creates radar chart data, and causes the display device 50 to display a radar chart in which a modulus of elasticity, a viscosity coefficient, and FIB-4 index are collectively arranged together in the upper side based on the generated radar chart data. In this case, a pentagon spreading upward represents the case of a liver cirrhosis.

As an example of a trend map, the display of a pentagon-based diagram, based on the statistical values of the items, has been described; however, the control circuitry 22 may generate diagram data for generating a blurred trend map, not a clear trend map, like a pentagon connected by lines.

Figure 24:
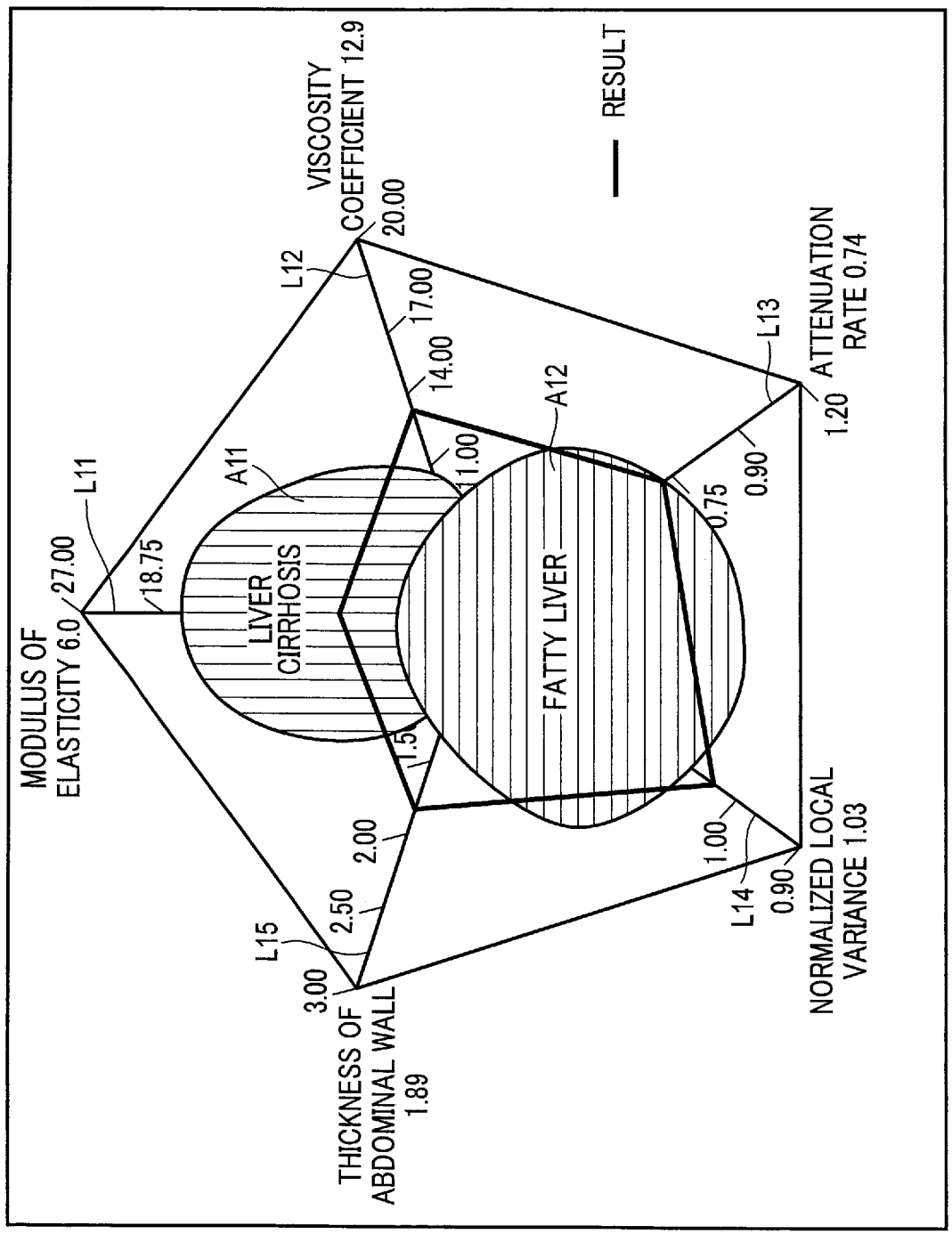
FIG. 24 is a diagram showing an example of a radar chart displayed on the display device according to the second modification.

FIG. 24 is a diagram showing an example of a radar chart displayed on the display device 50 of the second modification. According to the radar chart shown in FIG. 24, a first area A11 suspected of liver cirrhosis and a second area A12 suspected of fatty liver are shown on the radar chart. For example, the first area A11 and the second area A12 may be areas calculated from the statistical values of the items based on the diagnosis result of the ultrasound diagnostic apparatus 1. In FIG. 24, the boundary line of the first area A11 and the boundary line of the second area A12 are indicated by solid lines, but the boundary line may be a blurred boundary instead of a solid line. The first area A11 and the second area A12 may be expressed by filling colors for which the transmittance can be adjusted.

According to the second modification, the display of such various trend maps are utilized for the tissue characterization.

Second Embodiment

In the first embodiment, the diagram data (radar chart data) is generated in the ultrasound diagnostic apparatus 1 by using quantitative values of tissue properties that are acquired by the ultrasound probe 70 in a real-time manner; however, the embodiments of the invention are not limited thereto. In the second embodiment, a case where a medical imaging processing apparatus, such as a work station, generates quantitative values of tissue properties that are acquired from an external apparatus connected to the medical imaging processing apparatus via a communication network, such as a medical imaging diagnostic apparatus, will be described.

FIG. 25 is a block diagram showing an example of a configuration of an analysis system according to the second embodiment. The analysis system shown in FIG. 25 includes a medical imaging processing apparatus 80 and a medical imaging diagnostic apparatus 90. The medical imaging processing apparatus 80 and the medical image diagnostic apparatus 90 are connected to a local network to transmit information to a predetermined apparatus and to receive information transmitted from a predetermined apparatus. The analysis system may be connected to an external network, in addition to the local network or in place thereof.

The medical imaging processing apparatus 80 includes input interface circuitry 81, display circuitry 82, communication interface circuitry 83, memory circuitry 84, and processing circuitry 85.

The input interface 81 is implemented, for example, by a mouse, keyboard, or a touch pad in which an instruction is input by contact to an operation surface. The input interface 81 accepts, for example, an instruction to start a tissue characterization from an operator.

The display circuitry 82 has a display device, such as a CRT (cathode-ray tube) display, a liquid crystal display, an organic EL (electroluminescence) display, an LED display, or a plasma display, etc. The display circuitry 82 may be a touch panel or a TCS. The display circuitry 82 is connected to the processing circuitry 85 and externally displays a signal supplied from the processing circuitry 85. The display circuitry 82 displays a diagram, etc. based on diagram data supplied from the control circuitry 85, for example.

The communication interface circuit 83 performs data communication with the medical imaging diagnostic apparatus 90 and the external apparatus 91, which are connected to a network, etc. shown in FIG. 25.

The memory circuitry 84 includes, for example, a magnetic or optical storage medium, or a processor-readable storage medium such as a semiconductor memory. The memory circuitry 84 stores a control program for realizing various functions according to the present embodiment. The memory circuitry 84 stores a plurality of thresholds for respective types of tissue properties in advance.

The processing circuitry 85 is a processor acting as a nerve center of the medical imaging processing apparatus 80, for example. The processing circuitry 85 performs an operation program stored in the memory circuitry 84 to realize a function corresponding to the operation program. Specifically, the control circuitry 85 has a quantitative value acquisition function 851, a diagram data generation function 852, and a display control function 853.

The quantitative value acquisition function 851 is a function of acquiring quantitative values of tissue property parameters of a subject's region of interest. When the quantitative value acquisition function 851 is executed, the processing circuitry 85 obtains, via the communication interface circuitry 83, for example, ultrasound image data (including B-mode image data and tissue property image data) stored in the medical imaging diagnostic apparatus 90 or in the external apparatus 91, which will be described later. The processing circuitry 85 sets a region of interest and calculates a representative value, etc. by using acquired ultrasound image data. It is thereby possible to obtain quantitative values of tissue properties based on the acquired ultrasound image data. The processing circuitry 85 may obtain, for example, a quantitative value of a predetermined type of tissue properties from the medical imaging diagnostic apparatus 90 via the communication interface circuitry 83.

The diagram data generation function 852 is a function for generating a diagram of a region of interest based on a plurality of types of quantitative values obtained by the quantitative value acquisition function 851. When the diagram data generation function 852 is executed, the processing circuitry 85 generates diagram data as tissue characterization support information by using the plurality of types of quantitative values of tissue properties obtained from the region of interest of the subject P, and threshold values that are set for the plurality of types of tissue properties.

The display control function 853 is a function for displaying diagram data, etc. generated by the diagram data generation function 852. When the display control function 853 is executed, the processing circuitry 85 causes the display device 50 to display the diagram generated based on the diagram data. The control circuitry 85 may generate a graphical user interface (GUI) through which an operator (for example, a diagnostician) inputs various instructions by the input interface circuitry 81, and directs the display 82 to display the generated GUI.

The medical imaging diagnostic apparatus 90 is an apparatus capable of obtaining a predetermined medical image by performing scanning on a subject. The medical imaging diagnostic apparatus 90 is an ultrasound diagnostic apparatus, an MRI apparatus, a CT apparatus, or a nuclear medicine diagnostic apparatus. In the second embodiment, let us suppose that the medical imaging diagnostic apparatus 90 is an ultrasound diagnostic apparatus.

The external apparatus 91 is, for example, a picture archiving and communication (PACS) database which is a system that manages data of various medical images, or a database of an electronic medical record system which manages electronic medical records accompanied with medical images.

Figure 26:
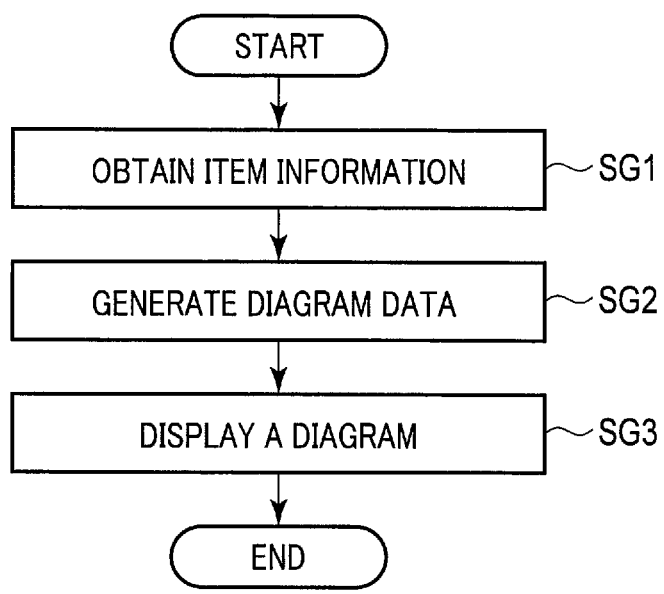
FIG. 26 is a flowchart showing operations of processing circuitry performed when the medical imaging processing apparatus according to the second embodiment generates a diagram related to a tissue characterization.

The operations of the medical imaging processing apparatus 80 according to the second embodiment will be described with reference to the flowchart of FIG. 26. FIG. 26 is a flowchart showing an example of the operations of processing circuitry 85 performed when the medical imaging processing apparatus 80 according to the second embodiment generates a diagram related to a tissue characterization. In the following description, let us suppose that the medical imaging diagnostic apparatus 90 obtains, in advance, ultrasound image data for obtaining quantitative values of a plurality of types of tissue properties. Let us also suppose that the obtained ultrasound image data is stored, in advance, in a memory circuit implemented in the medical imaging diagnostic apparatus 90. Also, let us suppose that the quantitative values of the plurality of types of tissue properties to be obtained are a modulus of elasticity, a viscosity coefficient, an attenuation rate, a normalized local variance, and a hepato-renal echo contrast. Let us further suppose that the portion targeted to the tissue characterization is a liver. The diagram is, for example, a radar chart based on radar chart data. Also, let us suppose that the tissue property parameters used to generate radar chart data are a modulus of elasticity, a viscosity coefficient, an attenuation rate, a normalized local variance, and a hepato-renal echo contrast. The obtained quantitative values of the plurality of types of tissue properties may be stored in an external apparatus other than the medical imaging diagnostic apparatus 90 connected to the medical imaging processing apparatus 80 via a network.

Upon the input of, for example, an instruction to conduct a tissue characterization for a liver via the input interface circuitry 81, the processing circuitry 85 executes the quantitative value acquisition function 851 to acquire B-mode image data stored in memory circuitry implemented in the medical imaging diagnostic apparatus 90 and ultrasound image data, such as tissue property image data, etc., via the communication interface circuitry 83. The processing circuitry 85 sets a region of interest and calculates a representative value, etc. for each of the types of tissue properties, by using the obtained ultrasound image data. Quantitative values of the plurality of types of tissue properties based on the obtained ultrasound image data are thus acquired (step SG1). Specifically, the processing circuitry 85 obtains a modulus of elasticity, a viscosity coefficient, an attenuation rate, a normalized local variance, and a hepato-renal echo contrast.

Upon obtaining a modulus of elasticity, a viscosity coefficient, an attenuation rate, a normalized local variance, and a hepato-renal echo contrast, the processing circuitry 85 executes the diagram data-generation function 852 to retrieve a plurality of thresholds that are respectively set for a modulus of elasticity, a viscosity coefficient, an attenuation rate, a normalized local variance, and a hepato-renal echo contrast, from the memory circuitry 84. The processing circuitry 85 then generates radar chart data as tissue characterization support information by using the acquired tissue property parameters and the thresholds respectively set for tissue properties (step SG2).

The processing circuitry 85 performs the display control function 853 to cause the display circuitry 82 to display a radar chart based on the generated radar chart data (step SG3).

According to the second embodiment, the processing circuitry 85 acquires quantitative values of the plurality of types of tissue properties relating to an ROI of the subject from the medical imaging diagnostic apparatus 90. That makes it possible to support a diagnostician to create electronic medical records, even when the medical imaging diagnostic apparatus 90 is not present near the diagnostician.

Other Embodiments

In the foregoing embodiments, the control circuitry 22 generates diagram data using quantitative values of tissue properties obtained by the ultrasound diagnosis apparatus; however, the embodiments are not limited thereto. For example, the control circuitry 22 may generate diagram data using a modulus of elasticity that can be obtained by the technology of MR elastography with the use of an MRI apparatus, and an X-ray attenuation rate that can be obtained by an X-ray CT apparatus.

In addition to the categories (items) related to tissue properties, such as a modulus of elasticity, a viscosity coefficient, an attenuation rate, a brightness ratio, a brightness dispersion, and a strain ratio, a BMI, a thickness of the abdominal wall, a result of blood test (alanine aminotransferase (ALT), aspartate aminotransferase (AST), γ-glutamyl transpeptidase (γ-GTP)) may be included in the diagram data to be generated. In this case, the categories are input by a user through an interface (or input by characters, or selected from candidates). The cut-off values are input by a user through the input device 60 (or input by characters, or selected from candidates). Either the categories or the cut-off values may be set in advance.

In the foregoing embodiments, a body part targeted for a tissue characterization is a liver; however, the embodiments are not limited thereto. For example, a tissue characterization may be performed to mammary glands. In this case, the control circuitry 22 acquires quantitative values of the plurality of types of tissue properties relating to mammary gland, and generates diagram data, such as radar chart data, using the acquired quantitative values.

Figure 27:
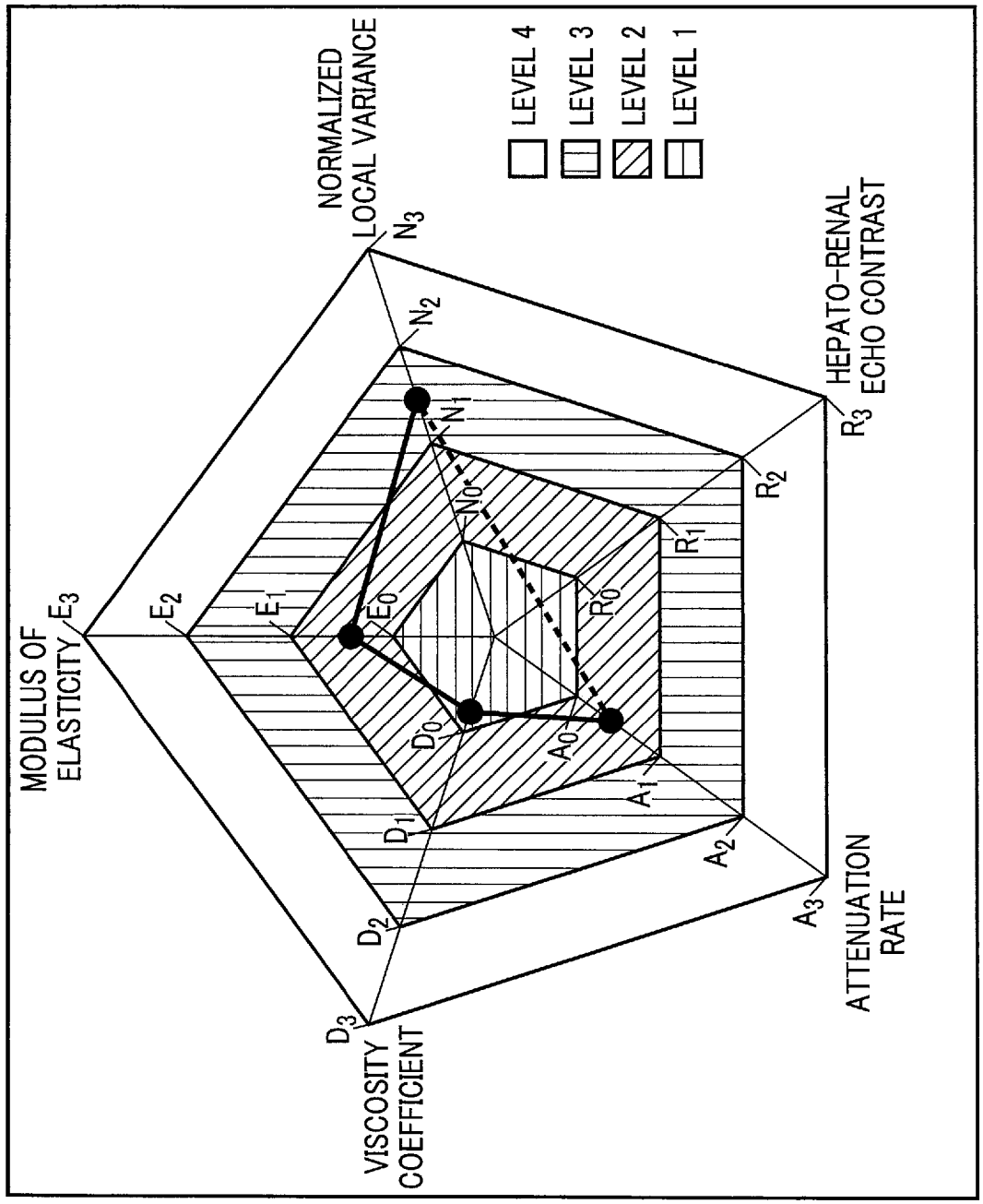
FIG. 27 is a diagram showing a radar chart according to other embodiments.

In the foregoing embodiments, when displaying a pentagonal radar chart, the control circuitry 22 displays the radar chart in which all the quantitative values of five types of tissue properties are reflected to the radar chart data; however, the embodiments are not limited thereto. For example, if the quantitative values of only four types of tissue properties are acquired, the tissue properties for which the quantitative values thereof are not obtained may not be displayed as points. FIG. 27 is a diagram showing an example of a radar chart in another embodiment. FIG. 27 shows a radar chart in a case where the quantitative value of a hepato-renal echo contrast is not acquired. According to FIG. 27, the quantitative value of the hepato-renal echo contrast is not plotted, and a line connecting the quantitative value of the attenuation rate with the quantitative value of the normalized local variance is displayed as a red dashed line, for example. On the other hand, the lines connecting the plotted points representing the other quantitative values are displayed as black solid lines. By thus displaying the line which crosses the line relating to the tissue property for which a quantitative value has not been obtained as a red dashed line, and not as a black solid line, it is possible to prevent a user from misunderstanding that the unobtained quantitative value is available.

In the foregoing embodiments, a pentagonal radar chart is displayed regardless of the types of the tissue properties for which the quantitative values are obtained; however, the embodiments are not limited thereto. For example, if the quantitative values of only four types of tissue properties are obtained, a square radar chart in which the four types of tissue properties are reflected may be displayed.

Figure 28:
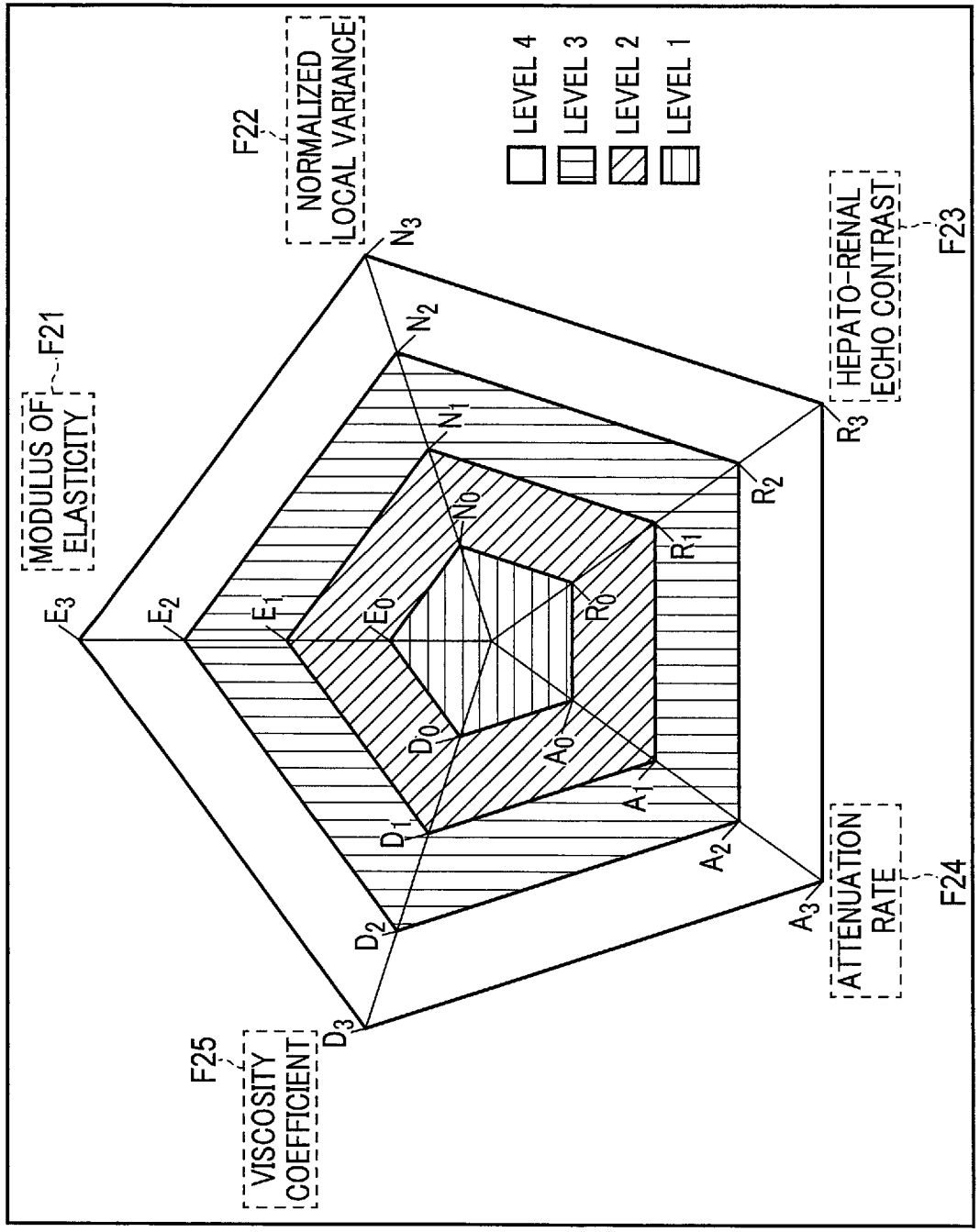
FIG. 28 is a diagram showing a tissue characterization support screen according to other embodiments.

In the foregoing embodiments, an order of acquiring the quantitative values of tissue property is predetermined; the embodiments are not limited thereto. FIG. 28 is a diagram showing an example of a tissue characterization support screen according to another embodiment. In FIG. 28, quantitative values of tissue properties are acquired for a region designated by the operator from the regions F21, F22, F23, F24, and F25. All the quantitative values of five types of tissue properties may be automatically acquired only by a single operation by the operator.

In the foregoing embodiments, the control circuitry 22 generates a diagram after acquiring all the quantitative values of five types of tissue properties; however, the embodiments are not limited thereto. For example, the control circuitry 22 first generates diagram data (e.g., radar chart data) in which the quantitative values of tissue properties are not reflected. The control circuitry 22 then updates the generated diagram data generated based on the acquired quantitative values, every time a quantitative value of one type of tissue properties is acquired. The control circuitry 22 may be configured to update the generated diagram data generated based on the acquired quantitative values, every time a quantitative value of one type of tissue properties is acquired, and to cause the display device 50 to display a diagram based on the updated diagram data.

In the foregoing embodiments, the control circuitry 22 generates diagram data (radar chart data) using quantitative values of tissue properties acquired by the ultrasound diagnosis apparatus in a single acquisition of quantitative values; however, the embodiments are not limited thereto. For example, diagram data may be generated using a mean of the quantitative values of the plurality of types of tissue properties that have been repeatedly acquired over a predetermined period of time, and a diagram based on the generated diagram data may be displayed.

In this case, the control circuitry 22 displays a diagram based on diagram data generated by using the quantitative values of the plurality of types of tissue properties acquired in the most recent acquisition of quantitative values, and a mean of the quantitative values obtained over the predetermined period of time. The control circuitry 22 generates diagram data in which a graph representing the most recently-acquired quantitative values and a graph of a mean of the quantitative values repeatedly acquired in the past are clearly distinguished from each other by using at least one or more types of lines and at least one or more colors in a diagram to be displayed.

In the foregoing embodiments, for example, the control circuitry 22 generates diagram data based on the quantitative values of the plurality of types of tissue properties, and displays a diagram based on the generated diagram data; however, the embodiments are not limited thereto. For example, the control circuitry 22 may be configured to search a similar case based on a graph shape formed by the quantitative values of tissue properties and/or tendency of the values (e.g., which tissue property corresponds to a prominent value/values). Specifically, data representing an appearance of a graph created from the quantitative values of tissue properties acquired in the past (past data), and case data which is associated with a definitive diagnosis result confirmed by a diagnostician based on the quantitative values, are stored in a predetermined database in advance. In this case, the thresholds to be set for the tissue properties are shared between a case where data representing a graph shape which is a search key is generated, and a case where data representing a graph shape of the past data is a search target.

The control circuitry 22 extracts case data having a similar graph shape by comparing the data representing a graph shape generated from the most recently-acquired quantitative values of tissue properties with the data representing a graph shape generated based on the past data. The control circuitry 22 displays a result of a definite diagnosis included in the extracted case data. It is thereby possible for the diagnostician to conduct a diagnosis based on the past data from an objective point of view. The data representing a graph shape which is used as a search key is accumulated in the database as new case data in which the data is associated with a result of diagnosis confirmed by a diagnostician's final judgment.

In the foregoing embodiments, the diagram data (radar chart data) generated by the ultrasound diagnostic apparatus 1 or the medical imaging processing apparatus 80 is used in the apparatus that generates the data; however, the embodiments are not limited thereto. The generated diagram data may be output to an external apparatus that creates electronic medical records, for example, via the communication interface circuitry 21 of the ultrasound diagnostic apparatus 1, or via the communication interface circuitry 83 of the medical imaging processing apparatus 80.

In the foregoing embodiments, the diagram data (radar chart data) generated by the ultrasound diagnostic apparatus 1 or the medical imaging processing apparatus 80 is displayed in the display device 50 or the display circuitry 82 as a diagram; however, the embodiments are not limited thereto. For example, if a region where an item indicating a predetermined tissue property is displayed is designated in the radar chart shown in FIG. 10, the control circuitry 22 or the processing circuitry 85 may display an image based on image data generated when the quantitative value of the tissue property is acquired, and/or a thumbnail of the image. This frees an operator from inconvenience due to the need of temporarily terminating a mode relating to a tissue characterization in order to check an image relating to a quantitative value of a tissue property, for example.

Elasticity image data and viscosity image data may be generated based on a common signal or common data. To generate elasticity image data and viscosity image data, it is necessary to transmit a push pulse at least one time and to transmit and receive a tracking pulse multiple times; for this reason, it takes more time to generate image data of one frame than to generate other image data. As described above, a diagnosis time is greatly shortened if the elasticity image data and the viscosity image data are generated based on a common signal or common data.

The acquisition of tissue property parameters required for generating a diagram and display of the diagram may be performed by a single-button operation. In this case, a region of interest for which a representative value, etc. of the tissue property parameters is acquired can be set if a user refers to, for example, B-mode image data or ultrasound image data, such as tissue property image data generated before a one-button operation. In this case, the set region of interest is fixed when the tissue property parameters are acquired. Alternatively, a region of interest may be automatically designated by analyzing B-mode image data or image data of at least one type of tissue property. For example, a dispersion of a brightness value of B-mode image data is locally calculated, and a region where the dispersion is relatively small is set as a region of interest. For example, a dispersion of a tissue property parameter of the tissue property image data is locally calculated, and a region where the dispersion is relatively small is set as a measurement region. The shape and size of the region of interest may be determined in advance and may be an ellipse or a rectangle; however, an entire region with a dispersion smaller than a threshold may be a region of interest.

The term "processor" used in the above explanation means, for example, circuitry such as a CPU (central processing unit), a GPU (graphics processing unit), an ASIC (application specific integrated circuit), or a programmable logic device (for example, an SPLD (simple programmable logic device), a CPLD (complex programmable logic device), or an FPGA (field programmable gate array)). The processor realizes its function by reading and executing the program stored in the memory circuitry. Each processor of the present embodiment is not limited to a case where each processor is configured as a single circuit; a plurality of independent circuits may be combined into one processor to realize the function of the processor. Furthermore, a plurality of constituent elements shown in FIGS. 1 and 12 may be integrated into one processor to implement the functions.

According to at least one of the embodiments described above, it is possible to present a plurality of types of tissue properties that have been quantified.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:
1. A medical imaging processing apparatus comprising:
processing circuitry configured to:
obtain quantitative values of a plurality of types of tissue properties relating to a region of interest of a subject;
generate a radar chart of the region of interest based on the quantitative values; and
cause to display the radar chart, wherein a modulus of elasticity, a viscosity coefficient, and an attenuation rate are arranged adjacent to each other in a discretionarily determined order in the radar chart.

2. The medical imaging processing apparatus according to claim 1, wherein tissue property parameters relating to the quantitative values of the plurality of types of tissue properties correspond to the modulus of elasticity, the viscosity coefficient, and the attenuation rate of the radar chart.

3. The medical imaging processing apparatus according to claim 2, wherein the processing circuitry is further configured to set at least two thresholds for each of the tissue property parameters when the radar chart is generated.

4. The medical imaging processing apparatus according to claim 3, wherein each of the thresholds has a unique range for each type of tissue properties.

5. The medical imaging processing apparatus according to claim 3, further comprising an interface circuitry configured to accept setting and changing of the tissue properties and the thresholds for the tissue properties.

6. The medical imaging processing apparatus according to claim 3, further comprising a memory configured to store the thresholds for the tissue properties respectively.

7. The medical imaging processing apparatus according to claim 3, wherein the processing circuitry is configured to cause to display each region divided by the thresholds, numbering at least two, in the radar chart in at least one or more colors.

8. The medical imaging processing apparatus according to claim 3, wherein the lines included in the radar chart are expressed as solid lines and/or multiple types of dashed lines.

9. The medical imaging processing apparatus according to claim 3, wherein a color of the lines displayed in the radar chart is at least one or more colors.

10. The medical imaging processing apparatus according to claim 3, wherein the radar chart includes a plurality of selection regions for selecting the tissue properties, and
upon designation of one selection region from the selection regions, the processing circuitry is configured to cause to display a medical image of tissue properties corresponding to the one selection region.

11. The medical imaging processing apparatus according to claim 3, wherein the processing circuitry is configured to cause to simultaneously display, along with the radar chart, or selectively display a thumbnail image that is generated when the quantitative values of the tissue properties are acquired.

12. The medical imaging processing apparatus according to claim 2, wherein the processing circuitry is configured to cause to display, in the radar chart, a first quantitative value group consisting of the quantitative values of the plurality of types of tissue properties, and a second quantitative value group consisting of the quantitative values of the plurality of types of tissue properties, the first quantitative value group being different from the second quantitative value group.

13. The medical imaging, processing, apparatus according to claim 12, wherein the second quantitative value group includes means calculated from the quantitative values of the plurality of types of tissue properties that have been acquired in the past, and
the processing circuitry is configured to cause to display the means for the tissue properties as points on the radar chart, and to display lines connecting the points respectively displayed for the tissue properties.

14. The medical imaging processing apparatus according to claim 1, wherein the processing circuitry is further configured to obtain, from an external apparatus, the quantitative value corresponding to at least one of the plurality of types of tissue properties.

15. The medical imaging processing apparatus according to claim 1, wherein the processing circuitry is further configured to update the radar chart every time the quantitative value is obtained.

16. The medical imaging processing apparatus according to claim 1, wherein the processing circuitry is further configured to generate workflow information indicating procedure of obtaining the quantitative values of the plurality of types of tissue properties.

17. The medical imaging processing apparatus according to claim 1, wherein the quantitative values include a modulus of elasticity, a viscosity coefficient, an attenuation rate, a brightness dispersion, and a strain ratio.

18. The medical imaging processing apparatus according to claim 1, wherein the processing circuitry is further configured to output the radar chart to an external apparatus.

19. The medical imaging processing apparatus according to claim 1, further comprising a scanner configured to perform scanning to the region of interest, wherein
the processing circuitry is further configured to acquire the quantitative value corresponding to at least one of the plurality of types of tissue properties by analyzing a result of the scanning.

20. The medical imaging processing apparatus according to claim 19, wherein the medical imaging processing apparatus is any of an ultrasound diagnosis apparatus, an X-ray CT apparatus, or an MRI apparatus.

21. The medical imaging processing apparatus according to claim 1, wherein the processing circuitry is configured to generate the radar chart with an arrangement of the quantitative values of tissue properties shown on the radar chart, the arrangement being based on information regarding a relationship among the quantitative values of the plurality of types of tissue properties.

22. The medical imaging processing apparatus according to claim 21, wherein the processing circuitry is configured to generate the radar chart such that, among the quantitative values of the plurality of types of tissue properties, the modulus of elasticity relating to an index indicating a stiffness of tissue and the viscosity coefficient relating to an index indicating viscosity of tissue are adjacently displayed on the radar chart.

23. The medical imaging processing apparatus according to claim 21, wherein the processing circuitry is configured to generate the radar chart such that, among the quantitative values of the plurality of tissue properties, the attenuation rate relating to an index indicating a degree of ultrasound attenuation in the subject's tissue and a quantitative value relating to a degree of dispersion of signals reflected in the subject's tissue are displayed adjacently to each other on the radar chart.

24. The medical imaging processing apparatus according to claim 23, wherein the region of interest is a liver,
the processing circuitry is configured to:
acquire a thickness value of an abdominal wall of the subject; and
generate the radar chart based on the quantitative values and the thickness value of the abdominal wall, wherein
the radar chart is generated in such a manner that, among the quantitative values of the plurality of types of tissue properties, two or more of the attenuation relating to an index indicating a degree of ultrasound attenuation in the subject's tissue, a quantitative value relating to a degree of dispersion of signals reflected in the subject's tissue, and the thickness value of the abdominal wall are displayed adjacently to each other on the radar chart.

25. The medical imaging processing apparatus according to claim 1, wherein the processing circuitry is further configured to generate the radar chart that includes information corresponding to a specific case.

26. The medical imaging processing apparatus according to claim 1, wherein the viscosity coefficient is arranged between the modulus of elasticity and the attenuation rate in the radar chart.

* * * * *